(12) United States Patent
Singh et al.

(10) Patent No.: US 6,569,847 B1
(45) Date of Patent: May 27, 2003

(54) SUBSTITUTED AZETIDIN-2-ONES AS CYSTEINE PROTEASE INHIBITORS

(75) Inventors: Rajeshwar Singh, Edmonton (CA); Andhe V. Narender Reddy, Edmonton (CA); Jadwiga Kaleta, Edmonton (CA); Ronald G. Micetich, Edmonton (CA); Mark Whittaker, Abingdon (GB); Philip Huxley, Freeland (GB)

(73) Assignee: NAEJA Pharmaceuticals Inc., Edmonton (CA)

( * ) Notice: Subject to any disclaimer, the term of this patent is extended or adjusted under 35 U.S.C. 154(b) by 0 days.

(21) Appl. No.: 09/958,141

(22) PCT Filed: Apr. 3, 2000

(86) PCT No.: PCT/GB00/01261

§ 371 (c)(1),
(2), (4) Date: Oct. 5, 2001

(87) PCT Pub. No.: WO00/59881

PCT Pub. Date: Oct. 12, 2000

(30) Foreign Application Priority Data

Apr. 6, 1999 (GB) ............................................. 9907683

(51) Int. Cl.$^7$ ................ C07D 205/085; C07D 205/095; A61K 31/397; A61P 21/00; A61P 19/00
(52) U.S. Cl. .................. 514/210.02; 540/357; 540/359; 540/360
(58) Field of Search ............................... 540/357, 359, 540/360; 514/210.02

(56) References Cited

U.S. PATENT DOCUMENTS 5,905,076 A * 5/1999 Singh et al. ............ 514/210.06

FOREIGN PATENT DOCUMENTS

| WO | WO 96/32408 | 10/1996 |
| WO | WO 98/12176 | 3/1998 |
| WO | WO 98/12210 | 3/1998 |
| WO | WO 99/48911 | 9/1999 |

OTHER PUBLICATIONS

Academic Press Dictionary of Science and Technology (Morris, Academic Press, 1992) p. 38.*

* cited by examiner

*Primary Examiner*—Mark L. Berch
(74) *Attorney, Agent, or Firm*—Rothwell, Figg, Ernst & Manbeck

(57) ABSTRACT

This invention relates to substituted azetidin-2-ones and to pharmaceutical compositions containing such compounds. Their use in medicine as inhibitors of cysteine proteases, particularly the cathepsins is also described. The invention includes a compound of formula (I), Y represents —C(O)— or —S(O$_2$)—; R represents an allyl (ie CH$_2$=CHCH$_2$—) group or a radical. R$_1$ represents —OCOR$_5$, —OR$_5$, —SR$_5$, —S(O)R$_5$, or —S(O)$_2$R$_5$; R$_2$ represents a radical. R$_3$ represents —OR$_5$ or R$_5$; or a pharmaceutically acceptable salt, hydrate or solvate thereof.

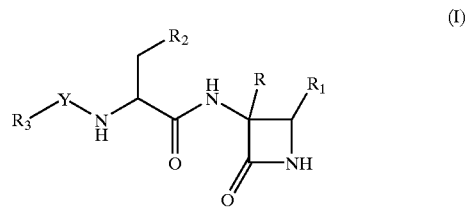

(I)

12 Claims, No Drawings

SUBSTITUTED AZETIDIN-2-ONES AS CYSTEINE PROTEASE INHIBITORS

CROSS-REFERENCE TO RELATED APPLICATION

This application is National Stage entry of International Application No. PCT/GB00/01261, filed Apr. 3, 2000, the entire specification claims and drawings of which are incorporated herewith by reference.

This invention relates to substituted azetidin-2-ones, to pharmaceutical compositions containing such compounds, and to their use in medicine as inhibitors of cysteine proteases, particularly the cathepsins.

BACKGROUND OF THE INVENTION

The cathepsin family (C1) of lysosomal cysteine (or thiol) proteases is a subset of the papain superfamily (clan CA of cysteine proteases) and includes cathepsin B, H, K, S, L and the recently discovered cathepsins O, O2/K, V, X, Z and W (lymphopain). Related enzymes also regarded as cysteine proteases are the cytoplasmic $Ca^{2+}$ dependent calpains (family C2). Cysteine proteases are classified both functionally and according to their active site, which has a thiol residue. They differ in substrate specificities and other enzymatic activities, these differences probably arising from evolutionary divergence.

The known cathepsins are synthesized on membrane bound ribosomes, transferred to the endoplasmic reticulum, then to the Golgi apparatus and finally to the lysosome and endosomes. They have an important function in regulation of intracellular protein metabolism, mobilisation of tissue proteins and conversion of proenzymes, prohormones and neuropeptides into biologically active molecules. The cathepsins are believed to be involved in a number of diseases.

Cathepsin K can be secreted into the extracellular space and is involved in bone and cartilage remodelling. Cathepsin K is implicated in the pathogenesis of osteoporosis. Cathepsin K inhibitors can prevent osteoporosis in animal models (PNAS. 1997. 94:14249–14254). Cathepsin L inhibitors have also been shown to inhibit osteoporosis (Bone, 1997. 20:465–471).

Cathepsin B and others have also been shown to be released extracellularly by various tumour cells and are thought to play a role in tumour invasion (Journal of cellular Physiology. 1992. 150:534–544).

The cathepsins have also been shown to play a role in rheumatoid arthotis (Arthritis and Rheumatism 1994. 37:236–247) and neuronal and cardiac ischaemia (European Journal of Neuroscience. 1998. 10.1723–1733).

Cathepsins S and L both play a role in the generation of free MHC class II molecules capable of binding antigenic peptides in the endosomes. These class II/peptide complexes move to the cell membrane and are involved in T lymphocyte activation. Inhibitors of Cathepsin S have been shown to inhibit allergic immune responses (Journal of Clinical Investigation. 1998. 101:2351–2363).

In addition to their role in the above diseases, cathepsins play a major role in the pathogenesis of infectious diseases. For example, cathepsins are used by the protozoal parasites Plasmodium (malaria) and Trypanosoma (Chagas Disease) to invade the human host and cathepsin inhibitors can inhibit experimental disease in both cases (Antimicrobial agents and chemotherapy. 1998. 42:2254–2258; Journal of Experimental Medicine. 1998. 188:725–734). Cathepsins are also virulence factors for several pathogenic bacteria.

A recent review (Annu. Rev. Physiol. 1997. 59:63–88) describes the state of the art of cysteine proteases, including the cathepsins, and their presumed biological functions. Another review (Exp. Opin. Ther. Patents, 1998, 8(6), pp645–672) deals with cathepsin B inhibitors as potential anti-metastatic agents.

International patent applications WO 96132408, WO 98/12176, WO 98/12210 and GB 9806287.0 describe, inter alia, classes of cysteine protease inhibitors which may be represented by formula (IA):

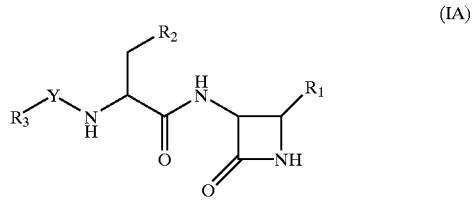

wherein Y, $R_1$, $R_2$ and $R_3$ represent the groups found in corresponding positions of the compounds disclosed in those publications. These known compounds are azetidin-2-ones which are monosubstituted at positions 3 and 4.

BRIEF DESCRIPTION OF THE INVENTION

The present invention makes available a new class of cysteine protease inhibitors which differ in structure from those disclosed in WO 96/32408, WO 98/12176, WO 98/12210 and GB 9806287.0 principally in that they are disubstituted at the 3-position. These compounds are useful for the treatment of diseases mediated by cysteine protease activity, for example muscular dystrophy, osteoporosis, tumour metastasis, rheumatoid arthritis, neuronal or cardiac ischaemia, allergic immune response, and protozoal or bacterial disease.

DETAILED DESCRIPTION OF THE INVENTION

According to the present invention, there is provided a compound of formula (I)

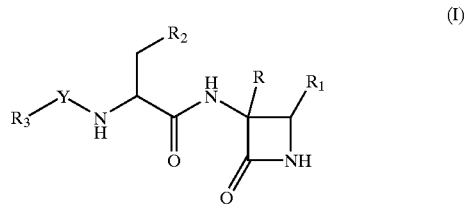

Y represents —C(O)— or —S(O$_2$)—;

R represents an allyl (ie CH$_2$=CHCH$_2$—) group or a radical of formula R$_4$-(ALK)$_p$-(Z)$_n$-(ALK)$_q$- wherein Z represents —O— or —S—, ALK represents a divalent C$_1$–C$_3$alkyl or halogen-substituted C$_1$–C$_3$alkyl radical, R$_4$ represents hydrogen or halogen, or an optionally substituted phenyl group, and n, p and q are independently 0 or 1, PROVIDED THAT (i) when R$_4$ is hydrogen and both p and n are 0 then q is 1; and (ii) when R$_4$ is halogen and n is 1 then p is 1; and (iii) when R$_4$ is halogen then p, n and q are not all 0;

R$_1$ represents —OCOR$_5$, —OR$_5$, —SR$_5$, —S(O)R$_5$, or —S(O)$_2$R$_5$;

R$_2$ represents a radical of formula R$_6$-(ALK)$_p$-(Z)$_n$-(ALK)$_q$- wherein p, Z and ALK are as defined in relation to R, q is 0 or 1, n is 0 or 1 when q is 1 and n is 0 when q is 0, and $R_6$ is hydrogen or an optionally substituted $C_1$–$C_6$alkyl, $C_2$–$C_6$alkenyl, $C_2$–$C_6$alkynyl, cycloalkyl, cycloalkenyl, aryl or heterocyclic group; or $R_2$ together with the carbon atom to which it is attached forms a cycloalkyl ring;

$R_3$ represents —$OR_5$ or —$R_5$;

$R_5$ represents a radical of formula $R_7$—(A)$_t$— wherein t is 0 or 1; A represents (i) an optionally substituted divalent $C_1$–$C_6$alkyl, radical which may be interrupted by one or more non-adjacent —O—, —S— or —NH— linkages, or (ii) a divalent $C_2$–$C_6$alkenyl, $C_2$–$C_6$alkynyl, cycloalkyl, cycloalkenyl, aryl or heterocyclic radical, or (iii) a —NH— link; and $R_7$ represents hydrogen or an optionally substituted $C_1$–$C_6$alkyl, $C_2$–$C_6$alkenyl, $C_2$–$C_6$alkynyl, cycloalkyl, cycloalkenyl, aryl or heterocyclic group;

or a pharmaceutically acceptable salt, hydrate or solvate thereof.

Pharmaceutically acceptable salts of the compounds of this invention include the sodium, potassium, magnesium, calcium, hydrogen chloride, tartaric acid, succinic acid, fumaric acid and p-toluenesulfonic acid salts.

Preferably, the R and $R_1$ groups are cis to each other.

As used herein the term "($C_1$–$C_6$)alkyl" or "lower alkyl" means a straight or branched chain alkyl moiety having from 1 to 6 carbon atoms, including for example, methyl, ethyl, propyl, 1-methylethyl, butyl, 1-methylpropyl, 2-methylprop-1-yl, 2-methylprop-2-yl, pentyl, 3-methylbutyl, and hexyl. Similar terms such as "($C_1$–$C_3$) alkyl" are to be interpreted similarly.

As used herein the term "$C_2$–$C_6$alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl. Similar terms such as "($C_2$–$C_3$)alkenyl" are to be interpreted similarly.

As used herein the term "$C_2$–$C_6$ alkynyl" means a straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4pentynyl, 2-hexynyl, 3-hexynyl, 4-hexynyl and 5-hexynyl, Similar terms such as "($C_2$–$C_3$) alkynyl" are to be interpreted similarly.

As used herein the term "cycloalkyl" means a saturated alicyclic moiety having from 3–7 carbon atoms and includes, for example, cyclohexyl, cycloheptyl, cyclopentyl, cyclobutyl and cyclopropyl.

As used herein the term "halogen" means fluoro, chloro, bromo or iodo.

As used herein the term "aryl" refers to a mono-, bi- or tri-cyclic, substituted or unsubstituted, carbocyclic aromatic group, and to groups consisting of two covalently linked substituted or unsubstituted monocyclic carbocyclic aromatic groups. Illustrative of such groups are phenyl, biphenyl and napthyl. Examples include $C_6$–$C_{12}$ aryl groups such as phenyl, biphenyl, naphthyl, tetrahydronaphthyl, dihydronaphthyl, and cyclohexyl phenyl.

As used herein the unqualified term "heterocyclyl" or "heterocyclic" means a 5–7 membered heterocyclic ring, which may be aromatic or non-aromatic, containing one or more heteroatoms selected from S, N and O, and optionally fused to a benzene or hetero-atom containing ring. The term therefore includes $C_1$–$C_{11}$ heterocyclic groups containing 1–4 heteroatoms selected from nitrogen, sulfur or oxygen.

Examples include thienyl, pyridyl, 1,2,3-triazolyl, 1,2,4-triazolyl, 1,2,3,4-tetrazolyl, imidazolyl, quinolinyl, isoquinolinyl, indolyl, pyrimidinyl, benzofuranyl, benzothienyl, morpholinyl, thiomorpholinyl, piperazinyl, piperidinyl, tetrahydroquinolinyl, tetrahydroisoquinolinyl, pyridylphenyl, pyrimidylphenyl, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimrdazolyl, maleimido, succinimido, and phthalimido groups.

As used herein, the unqualified term "substituted" as applied to a group or radical means substituted with 1, 2, or 3 substituents selected from ($C_1$–$C_3$)alkyl;

phenyl;

hydroxy or mercapto;

($C_1$–$C_3$)alkoxy or ($C_1$–$C_3$)alkylthio;

phenoxy or phenylthio;

halogen;

trifluoromethyl;

nitro;

cyano (—CN);

carboxyl, and amidated, esterified or protected carboxyl;

amino, mono- or di-($C_1$–$C_3$)alkylamino, or protected amino;

($C_1$–$C_3$)alkylcarbonyl- or ($C_1$–$C_3$)alkylcarbonylamino-; —CONHR$^A$, —NHR$^A$, —NR$^A$R$^B$, or —CONR$^A$R$^B$ wherein R$^A$ and R$^B$ are independently ($C_1$–$C_3$)alkyl; and —NH—C(=NR$_8$)R$_9$ wherein $R_9$ is amino, mono- or di-($C_1$–$C_6$)alkylamino, protected amino, or ($C_1$–$C_3$) alkyl, and $R_8$ is hydrogen, ($C_1$–$C_3$)alkyl, or an N-protecting group.

As used herein the term "protecting group" when used in relation to an amino or carboxylic acid moeity in the compounds of this invention means a group which is used to render the amino or carboxylic acid moeity substantially non reactive, ie to neutralise its amino or carboxylic acid functionality. In this context, protected amino groups include amido and acylamino, protected hydroxy or mercapto groups include ethers and thioethers, protected carboxyl groups include esters, and imidazolyl, indolyl or guanidyl groups may be protected as t-butoxycarbonyl derivatives. These are only examples of the many protecting derivatives known in the art, and others will be known to the skilled man. Such protecting groups are of course well known, eg from the art of peptide synthesis, and are discussed in the widely used handbook by T. W. Greene and P. G. M. Wuts, Protective groups in Organic Synthesis, 2nd Edition, Wiley, New York 1991, and elsewhere in the chemical literature.

The azetidinone nucleus in the compounds of the invention has two asymmetric carbon atoms at position 3 (carrying the R group) and 4 (carrying the $R_1$ group), and can exist as 4-diastereoisomers. While the invention includes all such diastereomers and mixtures thereof (including racemic mixtures), compounds in which the R and $R_1$ groups are cis to each other are currently preferred, as are mixtures of diastereoisomers in which that configuration predominates.

As mentioned above, the compounds of the invention differ in structure from those of WO 96/32408, WO 98/12176, WO 98/12210 and GB 9806287.0 principally in that they carry a second substituent R at the 3-position of the azetidin-2-one ring. Thus the substituents $R_1$, $R_2$ and $R_3$ in the compounds of the invention may be any of the groups falling within the above definitions of $R_1$, $R_2$ and $R_3$ and which are present in corresponding positions of cysteine protease inhibitors disclosed in those patent applications. Without prejudice to the generality of the foregoing, in the compounds of the invention:

Y may be, for example, —C(O)—;

R may be, for example, allyl, methyl, ethyl, n-propyl, n-or iso-butyl, methyoxymethyl, ethoxymethyl, benzyl, or phenoxymethyl;

$R_1$ may be, for example, acetoxy; butyloxy; 2-carboxyethyloxy; 2-aminoethyloxy; 2-fluoroethoxy; cyclopentyloxy; cyclohexyloxy; cyclohexylthio; phenoxy, phenoxy substituted by methyl, tert-butyl, trifluoromethyl, amino, hydroxy, acetamido, cyano, carboxy or fluoro; naphthyloxy; morpholino-phenyloxy; 2-hydroxyethylthio; phenylthio; phenylsulphonyl; 4-(2-carboxy-2-amino ethylyphenoxy; 2-pyridylthio; 4-pyridylthio; benzyloxy; 3-pyridyl-phenoxy; 3-tetrazolyl-phenoxy; 3,4-methylenedioxy-phenoxy; 3,4ethylenedioxy-phenoxy; tetrahydroquino-linoxy; quinolinoxy; or quinolinthio. Currently preferred are acetoxy and phenoxy.

$R_2$ may be, for example, a phenyl group which may be substituted by one or more of hydroxy, halogen, methoxy, methyl, isopropyl, tert-butyl and trifluoromethyl; isopropyl, cyclohexyl; 3-pyridinyl; naphthyl; biphenyl; 2-thienyl; 3,4-methylenedioxyphenyl; 3,4-ethylenedioxy-phenyl; benzothienyl; thiazolyl; quinolinyl; isoquinolinyl; tetrahydroquinolinyl; tetrahydronaphthyl; aminonaphthyl; or acetamidonaphthyl. Presently preferred are phenyl, isopropyl, cyclohexyl and 3-pyridinyl.

$R_3$ may be, for example, benzyloxy, 3-phenylpropyloxy, 3-phenylpropyl, 3-phenylprop-1-enyl, 6-N,N-dibenzyloxycarbonylguanidino-hexyl, 6-guanidino-hexyl, methoxy-methyleneoxy-methyl, 2-amino-ethoxy-methyl, 3-(pyridin-3- or 4-ylypropyl, or 3-(pyridin-3- or 4-ylprop-1-enyl.

Specific compounds of the invention include those of named and characterised in the Examples herein.

As stated, the compounds of the invention are inhibitors of cysteine proteases, for example cathepsins B, L, S and/or K. The invention therefore also provides a pharmaceutical composition containing a compound of formula (I) as defined above, and a pharmaceutically acceptable carrier. Also provided is the use of such a compound in the preparation of a composition for inhibiting cysteine protease activity in the body of a mammal suffering a disease mediated by such activity, and a method of treatment of an animal suffering from a disease mediated by cysteine protease activity, which method comprises administering to the mammal a sufficient amount of a compound of formula (I) as defined above to inhibit such activity.

Diseases mediated by cysteine protease activity include muscular dystrophy, osteoporosis, tumour metastasis, rheumatoid arthritis, neuronal or cardiac ischaemia, allergic immune response, and protozoal or bacterial disease.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia;

non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations, which may be used for the drug, are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as local anaesthetic, preservative and buffering agents can be dissolved in the vehicle. Intravenous infusion is another route of administration for the compounds.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Compounds of the invention may be prepared by acylation of the 3amino group of a compound of formula (II) with an acylating derivative of a compound of formula (III)

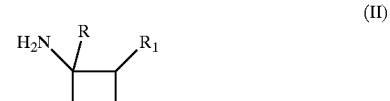

(II)

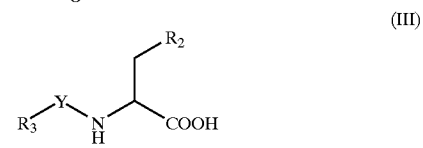

(III)

wherein Y, R, $R_1$, $R_2$ and $R_3$ are as defined above except that any functional groups present in R, $R_1$, $R_2$ and $R_3$ which might give rise to substantial amounts of unwanted by-products are protected, and thereafter removing any such protecting groups. In the acylation reaction, compound (III) may be activated as an active ester, for example the hydroxybenzotriazolyl ester, to facilitate the acylation reaction.

Compounds (II) are accessible from commercially available materials by widely known synthetic methods. Reaction Schemes 1 and 2 below illustrate synthetic routes to compounds (II) in which R is methyl, which may be modified as appropriate to produce other compounds of formula (II). Compounds (III) are in many cases commerially available, and otherwise are also accessible from commercially available materials by widely known synthetic methods.
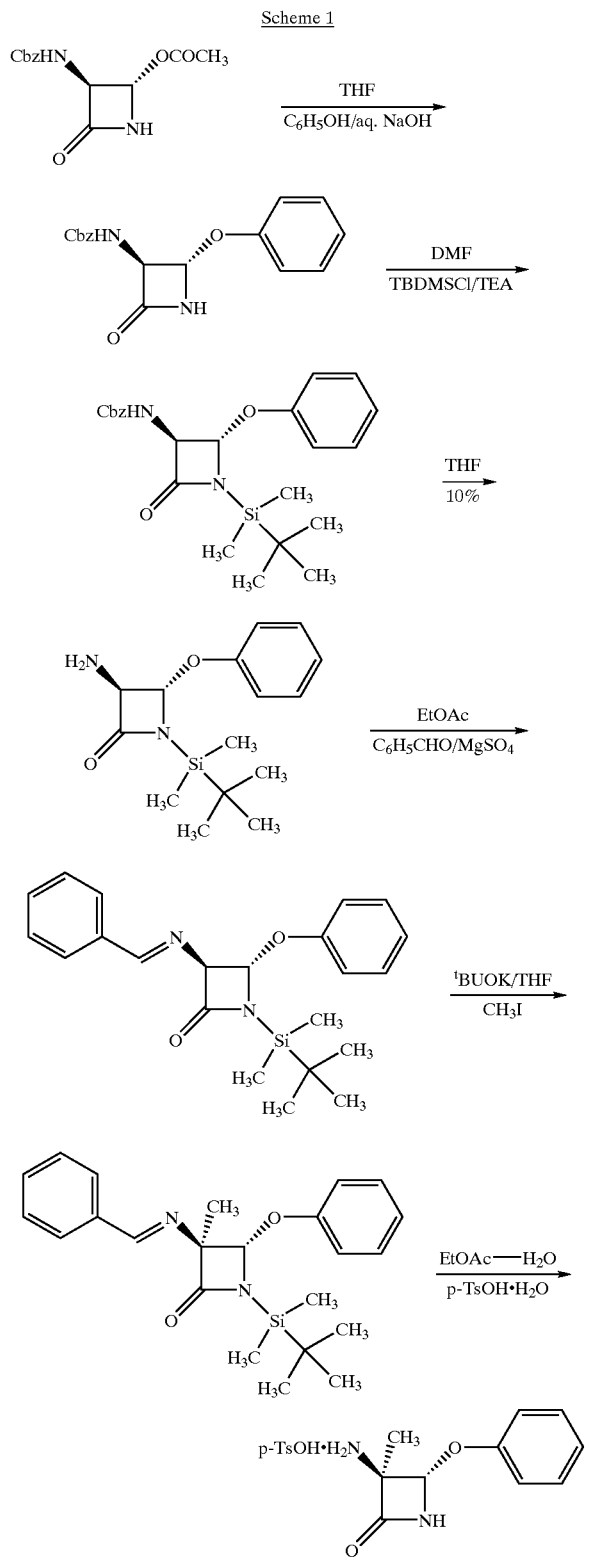
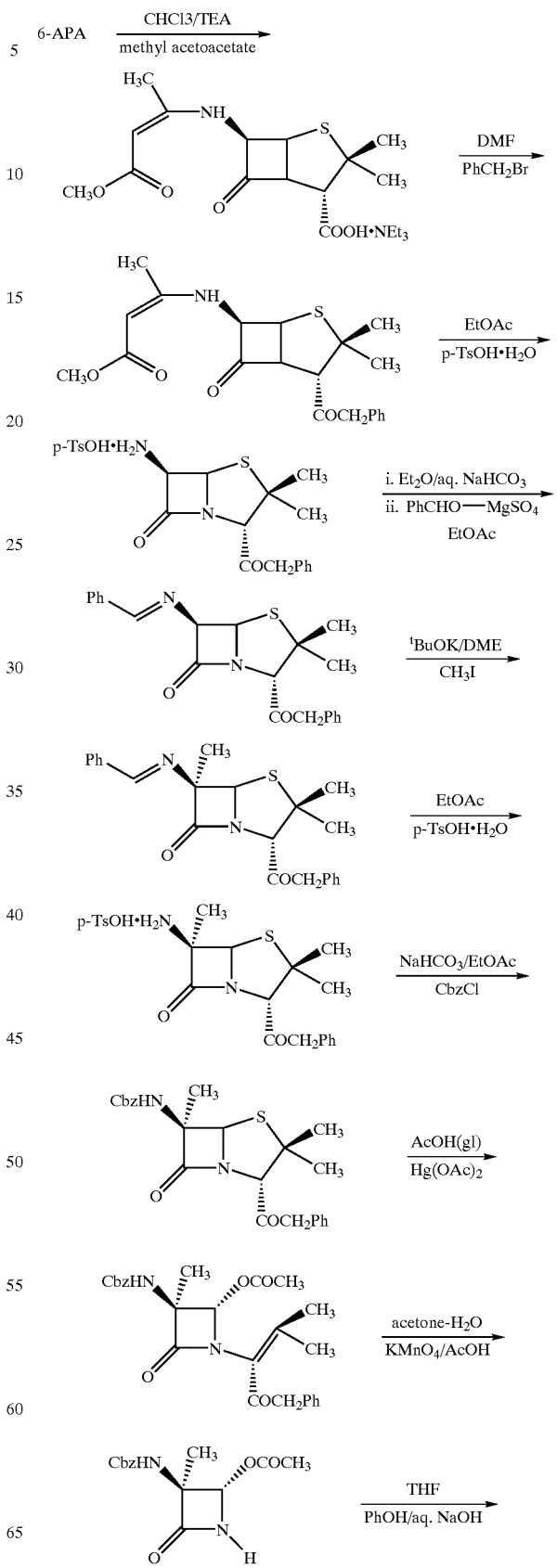

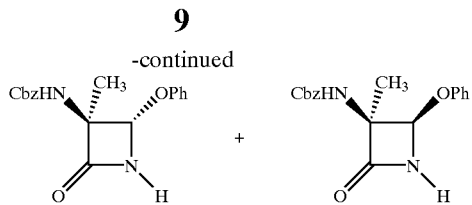

An example of an acylation reaction between a compound of formula (II) and a compound of formula (III) is shown in Scheme 3. In general, the amine (II) and the acid (III) are coupled either in presence of coupling reagent or by use of the chloride or anhydride of (III) in presence of base or activated ester.

In some cases, compounds of formula (I) may be prepared by coupling a compound of formula (IV) with a compound of formula (V):

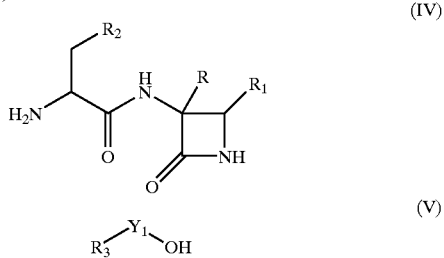

wherein $Y_1$ represents —CO— or —S(O)$_2$—, and R, $R_1$, $R_2$ and $R_3$ are as defined above except that any functional groups present in R, $R_1$, $R_2$ and $R_3$ which might give rise to substantial amounts of unwanted by-products are protected, and thereafter removing any such protecting groups. Here again the amine (IV) and the acid (V) ($Y_1$=—CO—) are coupled either in presence of coupling reagent or by use of the chloride or anhydride of (V) in presence of base, or by use of an activated ester.

Compounds (V) are in many cases commerially available, and otherwise are accessible from commercially available materials by widely known synthetic methods.

In some cases, one compound of formula (I) may be prepared from another of formula (I). For example, Scheme 3 shows a synthetic route in which the 4-acetoxy group in a compound of formula (I) wherein $R_1$ is acetoxy is converted to a group —$OR_5$ or —$SR_5$. Conversion of the 4-acetoxy group is effected by reacting with $R_5XH$ in presence of lewis acids such as zinc acetate, zinc iodide, zinc chloride, titanium tetrachloride, palladium acetate, boron trifluoride, aluminium trichloride and the like or in presence of base such as sodium hydroxide. Reactive groups in $R_5$ will of course be protected during such reactions, and subsequently deproteced. Thus, where a carboxy group is present in $R_5$ it may be protected with diphenyl methyl or 1,1-dimethyl ethyl and an amino group in $R_5$ may be protected with benzyloxycarbonyl or 1,1-dimethylethoxycarbonyl. Deprotection may be effected by hydrogenation or hydrolysis with acids.

Scheme 3

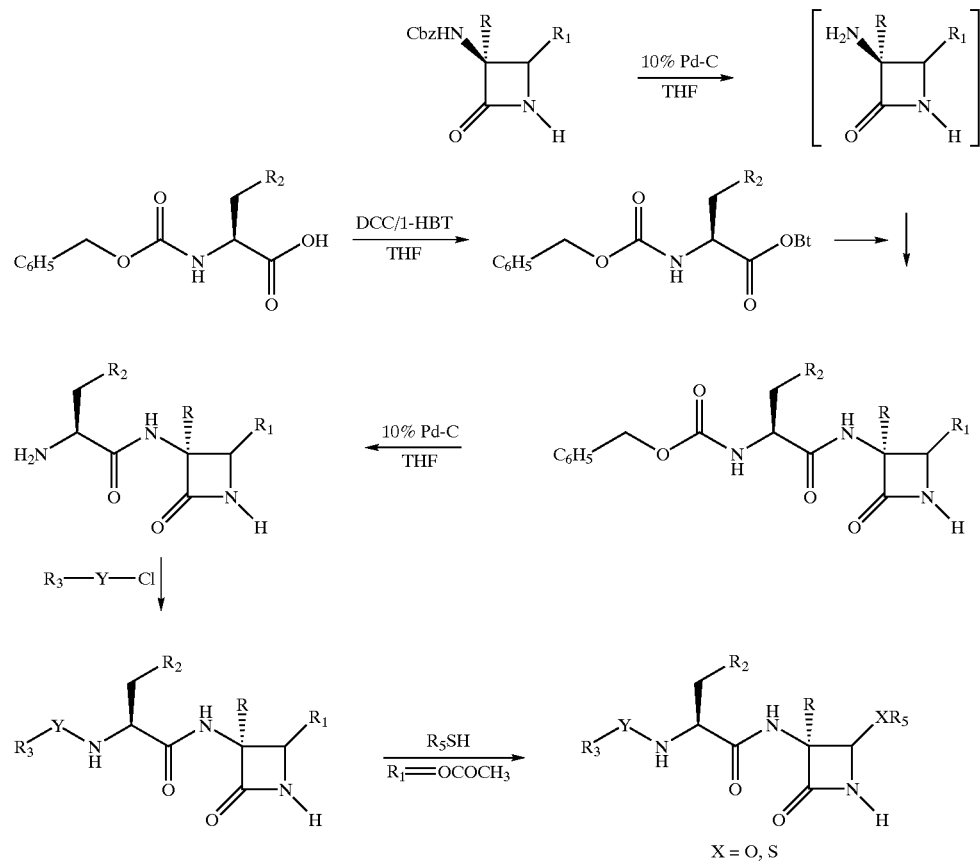

Monobactam derivatives of general formula I wherein $R_1$ is —$SR_5$ may be converted to, —$SOR_5$, or —$SO_2R_5$ by oxidation with oxidizing agent such as m-chloroperbenzoic acid, hydrogen peroxide peracetic acid, potassium permanganate, or manganese dioxide.

The following Examples illustrate embodiments of the invention.

EXAMPLE-1

(3S,4S)-3-[2S-2-(benzyloxycarbonylamino)-2-benzyl]-acetamido-3-methyl-4-phenoxy-azetidine-2-one Step-1: (3S,4S)-1-(N-tert-butyldimethylsilyl)-3-benzyloxycarbonylamino-4-phenoxy-azitidine-2-one A solution of 3-(S)-benzyloxycarbonylamino-4-(R)-phenoxy-azitidine-2-one (5.05 g, 16.17 mmol) in dry dimethyl formamide (50 ml) under nitrogen was treated with tert-butyl dimethylsilyl chloride (2.93 g, 19.40 mmol) at room temperature. The reaction mixture was added with triethyl amine (2.454 g, 24.3 mmol) with in 10 min. and stirred at room temperature for 1.5 h. The suspension obtained was filtered and the filtrate was concentrated in vacuo to give a gummy mass. The gum obtained was dissolved in ethyl acetate (200 ml), washed with water (2×100 ml), brine (100 ml), dried over magnesium sulfate, filtered and evaporated in vacuo to give the crude product as a foamy gum. Purification of the above crude product over silica gel column using a mixture of hexane:ethyl acetate (9:1) gave the pure compound as a viscous oil (6.1 g).

Yield: 88.4%.

$^1$H NMR (DMSO-$d_6$): δ0.23 and 0.26(2s, 6H), 0.97(s, 9H), 4.44(d, 1H, J=9.0 Hz), 5.11(ABq, 2H, J=1.0 and 13.9.0 Hz), 5.55(s, 1H, C4H), 6.82–7.39(m, 10H) and 8.35(d, 1H, 8.3 Hz)

Step-2: (3S,4S)-1-(N-tert-butyldimethylsilyl)-3-amino-4-phenoxy-azetidine-2-one (3S,4S)-1-(N-tert-butyldimethylsilyl)-3-benzyloxycarbonylamino-4-phenoxy-azitidine-2-one (7.77 g, 18.22 mmol) and 10% Pd-C (50% wet, 7.7 g) in a mixture of EtOAc-THF (1:1, 200 ml) was hydrogenated at 344, 737.85 N/m$^2$ (50 psi) for 2.5 hrs and filtered through Celite. The filtrate was evaporated in vacuo and dried over the pump to give a clear, sticky oil, which was purified over a small silica gel column using hexane: EtOAc (8:2 to 1:1) to give pure compound (4.89 g) as an oil.

Yield: 91.8%.

$^1$H NMR (DMSO-$d_6$): δ0.18 and 0.26(2s, 6H), 0.96(s, 9H), 2.55(s, 2H), 3.88(t, 1H, J=8.6 Hz), 5.15(d, 1H, J=0.9 Hz) and 6.97–7.38(m, 5H).

Step-3: (3S,4S)-1-(N-tert-butyldimethylsilyl)-3-benzylideneimino-4-phenoxy-azitidine-2-one To a suspension of (3S,4S)-1-(N-tert-butyldimethylsilyl)-3-amino-4-phenoxy-azitidine-2-one (4.89 g, 16.72 mmol) in dry benzene (80 ml) and magnesium sulfate (anhyd., 20 g.) was added benzaldehyde (1.952 g, 18.393 mmol) and the mixture was stirred under nitrogen for 24 hrs. The suspension was filtered and the filtrate was evaporated in vacuo to give an oil, which was dissolved in EtOAc (200 ml). The EtOAc solution was washed with water (2×150 ml), sodium bisulfite (10%, 2×150 ml), brine (200 ml), dried over magnesium sulfate, filtered and evaporated in vacuo to give the title compound as a thick and clear oil (6.2 g).

Yield: 97.5%.

$^1$H NMR (DMSO-$d_6$): δ0.25 and 0.30(2s, 6H), 0.99(s, 9H), 4.91(s, 1H), 5.73(s, 1H), 6.85–7.85(m, 10H) and 8.51 (s, 1H).

Step-4: (3S,4S)-1-(N-tert-butyldimethylsilyl)-3-benzylideneimino-3-methyl-4-phenoxy-azitidine-2-one (3S,4S)-1-(N-tert-butyldimethylsilyl)-3-benzylideneimino-4-phenoxy-azitidine-2-one (2.017 g, 5.3 mmol) in dry THF under nitrogen was cooled to −40° C. and treated with potassium-tert-butoxide (0.654 g, 5.8302 mmol) in one portion. After stirring for 15 min., was added methyl iodide (0.828 g, 5.8302 mmol) to the orange-red colored reaction mixture and was stirred for 20 min. at −40° C. The reaction mixture was quenched with 2 ml of sat. ammonium chloride solution, stirred for 5 min. and diluted with ethyl acetate (100 ml). The EtOAc solution was washed with water (2×10 ml), brine solution (100 ml), dried over anhydrous magnesium sulfate, filtered and evaporated in vacuo to give a gum, which was purified over a silica gel column at ~10° C., using a mixture of hexane:ethyl acetate (4:1) to give the pure compound as an oil (0.498 g).

Yield: 23.8%.

$^1$H NMR (DMSO-$d_6$): δ0.20 and 0.26(2s, 6H), 0.96(s, 9H), 1.37(s, 3H), 5.53(s, 1H), 6.97–7.88(m, 10H) and 8.63 (s, 1H).

Step-5: (3S,4S)-3-amino-3-methyl-4-phenoxy-azitidine-2-one. p-TsOH

To a solution of (3S,4S)-1-(N-tert-butyldimethylsilyl)-3-benzylideneimino-3-methyl-4-phenoxy-azitidine-2-one (0.528 g, 1.34 mmol) in ethyl acetate (15 ml) was added p-TsOH, H$_2$O, followed by dd. Water (3 ml). The reaction mixture was vigorously stirred at 35° C. for 4 h. and the resulting suspension was filtered, washed with cold EtOAc, ether and dried to give a white solid.

$^1$H NMR (DMSO-$d_6$): δ1.51 (s, 3H), 2.29(s, 3H), 5.64(s, 1H), 6.98–7.50(m, 9H), 8.94(br s, 3H) and 9.80(s, 1H).

Step-6: (3S,4S)-3-[2S-2-(benzyloxycarbonylamino)-2-benzyl-acetamido-]-3-methyl-4-phenoxy azetidin-2-one A mixture of N-carbobenzyloxy phenyl alanine (0.093 g, 0.31 mmol), DCC (0.064 g, 0.31 mmol) and 1-HBT (0.042 g, 0.31 mmol), in dry THF (10 ml) under nitrogen was stirred at room temperature for 1 h. The (3S,4S)-3-[2S-2-(benzyloxycarbonylamino)-2-benzyl-acetamido]-3-methyl-4-phenoxy azetidin-2-one. P-TsOH salt (0.107 g, 0.2936 mmol) was dissolved in DMF (8 ml) treated with triethyl amine (46 ul) and the clear solution obtained was added to the reaction mixture. After stirring for 1.5 h. the suspension was filtered and the filtrate was evaporated in vacuo to give a gummy crude product. The above gummy product was dissolved in EtOAc (80 ml), washed with aq. sat. NaHCO$_3$, brine solution, dried over anhydrous sodium sulfate, filtered and evaporated in vacuo. The crude product obtained was purified over silica gel column chromatography using a mixture of hexanes:ethyl acetate (1:1) to give the pure title compound (85 mg)

m.p.: 76.5–78° C.

$^1$H NMR (DMSO-$d_6$): δ1.32(s, 3H), 2.73–3.09(m, 2H), 4.35–4.45(m, 1H), 4.96(ABq, 2H, J=2.0 Hz), 5.56(s, 1H), 6.82–7.39(m, 15H), 7.56(d, 1H, J=8.8 Hz), 8.55(s, 1H) and 9.15(s, 1H).

EXAMPLE-2

(3S,4S)-3-[2S-2-(benzyloxycarbonylamino)-2-isopropyl]-acetamido-3-methyl-4-phenoxy azetidin-2-one A mixture of N-carbobenzyloxy leucine (0.083 g, 0.313 mmol), DCC (0.065 g, 0.313 mmol) and 1-HBT (0.043 g, 0.313 mmol), in dry DMF (10 ml) under nitrogen was stirred at room temperature for 1 h. (3S,4S)-3-amino]-3-methyl-4-phenoxy azetidin-2-one. p-TsOH salt (0.114 g, 0.313 mmol) was added to the reaction mixture followed by triethyl amine (48 ul, 0.035 g, 0.313 mmol) and stirred for an additional 3 h. The mixture was evaporated in vacuo and the crude product obtained was dissolved in EtOAc (80 ml), washed with water, brine solution, dried over anhydrous sodium sulfate, filtered and evaporated in vacuo to give the crude product. Purification of the above crude product by silica gel column chromatography using a mixture of hexanes:ethyl acetate (1:1) gave the pure title compound (88 mg)

Yield: 66.2%; m.p: 84.5–85° C.

$^1$H NMR (DMSO-d$_6$): δ0.88(d, 3H, J=6.2Hz), 0.91(d, 3H, J=6.4 Hz), 1.32(s, 3H), 1.00–1.80(m, 3H), 4.15–4.25(m, 1H), 5.03(ABq, 2H), 5.60(s, 1H), 6.85–7.35(m, 10H), 7.45 (d, 1H, J=8.5 Hz), 8.47(s, 1H), 9.12(s, 1H).

EXAMPLE-3

(3S,4S)-3-[2S-2-(N-benzyloxycarbonyl)-amino-2-isopropyl]-acetamido-3-benzyl-4-phenoxy azetidin-2-one

Step-1: (3S,4S)-1-(N-tert-butyldimethylsilyl)-3-benzylideneimino-3-benzyl-4-phenoxy-azitidine-2-one (3S,4S)-1-(N-tert-butyldimethylsilyl)-3-benzylideneimino-4-phenoxy-azitidine-2-one (1.622 g, 4.262 mmol) in dry THF under nitrogen was cooled to −60° C. and treated with potasium-tert-butoxide (0.574 g, 5.115 mmol) in one portion. After stirring for 15 min., was added benzyl bromide (0.8 g, 4.69 mmol) to the orange-red colored reaction mixture and was allowed to come to 0° C. over 30 min. The reaction mixture was quenched with ice-water and diluted with ethyl acetate (100 ml). The EtOAc solution was washed with water (2×10 ml), brine solution (100 ml), dried over anhydrous sodium sulfate, filtered and evaporated in vacuo to give a gummy oil (1.26 g).

Yield: 62.8%

Step-2: (3S,4S)-3-amino-3-benzyl-4-phenoxy-azitidine-2-one

To a solution of (3S,4S)-1-(N-tert-butyldimethylsilyl)-3-benzylideneimino-3-benzyl-4-phenoxy-azitidine-2-one (1.26 g, 2.68 mmol) in a mixture of ethyl acetate (20 ml) and water (10 ml) was added p-TsOH. H$_2$O (1.53 g, 8.03 mmol). The reaction mixture was vigorously stirred at r.t. for 48 h and the organic layer was separated. The aqueous layer was diluted with water (20 ml), washed with hexanes and freeze dried to give give the crude p-TsOH salt of (3S,4S)-3-amino-3-benzyl-4-phenoxy-azitidine-2-one which is contaminated with p-TsOH.

The above crude product was suspended in dd.H$_2$O (10 ml), adjusted to pH ~10 with aq.sat. NaHCO$_3$ and extracted with ethyl acetate (2×50 ml). The EtOAc extracts were pooled together, dried over anhydrous sodium sulfate, filtered and evaporated in vacuo to give 3-(S)-amino-3-benzyl-4-(R)-phenoxy-azitidine-2-one, as a white solid (0.36 g)

Yield: 50.1%; m.p.: 170–172° C.

$^1$H NMR (DMSO-d$_6$): δ2.05(s, 2H), 3.02(ABq, 2H, J=4.3 and 15.9), 5.41(s, 1H, C4H), 6.80–7.39(m, 10H) and 8.93(s, 1H).

Step-3: (3S,4S)-3-benzyloxy carbonylamino-3-benzyl-4-phenoxy azetidine-2-one A solution of (3S,4S)-3-amino-3-benzyl-4-phenoxy-azitidine-2-one (0.1 g, 0.373 mmol) in THF (8 ml) was treated with benzyloxy carbonyl chloride (0.072 g, 0.42 mmol) at room temperature and was added aq. NaHCO$_3$ (0.063 g, 0.746 mmol in 5 ml water). The resulting suspension was stirred vigorously at room temperature over 20 hrs., diluted with EtOAc (25 ml) and water (10 ml). The organic layer was separated, washed sequentially wih 1N. HCl (25 ml), aq. sat. NaHCO$_3$ (2×25 ml), brine solution and dried over anhydrous sodium sulfate. Evaporation of the solvent in vacuo gave a gummy mass, which was purified over silica gel column to give (3S,4S)-3-(N-benzyloxycarbonyl)-amino-3-benzyl-4-phenoxy azetidine-2-one (0.86 g).

Yield: 57%; m.p.: 64–65° C.

$^1$H NMR (DMSO-d$_6$): δ3.24(ABq, 2H, J=6.6 and 17.0), 4.95(d, 1H, J=12.9 Hz), 5.12(d, 1H, J=12.9 Hz), 5.34(s, 1H), 6.72–7.30(m, 15H), 7.72(s, 1H) and 9.02(s, 1H).

Step-4: 3(3S,4S)-3-[2S-2-(N-benzyloxycarbonyl)-amino-2-isopropyl]-acetamido-3-benzyl-4-phenoxy azetidin-2-one A mixture of (3S,4S)-3-(N-benzyloxycarbonyl)-amino-3-benzyl4-phenoxy azetidine-2-one (0.115 g, 0.43 mmol), N-carbobenzyloxy leucine (0.114 g, 0.43 mmol), DCC (0.089 g, 0.43 mol) and 1-HBT (0.058 g, 0.43 mmol) in dry THF (30 ml) under nitrogen was stirred at room temperature for 6 h. The suspension obtained was filtered and the filtrate was concentrated to give a gum, which was dissolved in EtOAc(80 ml), washed with aq. sat. NaHCO$_3$ (80 ml), brine solution, dried over anhydrous sodium sulfate, filtered and evaporated in vacuo to give the crude product. Purification of the above crude product by silica gel column chromatography using a mixture of hexanes:ethyl acetate (3:2) gave the pure title compound (0.075 g).

Yield: 34%; m.p.: 80.5–81.5° C.

$^1$H NMR (DMSO-d$_6$): δ0.80–0.88(m, 6H), 1.25–1.70(m, 3H), 3.24(d, 1H, J==11.0 Hz), 3.50(d, 1H, J=11.0 Hz), 4.10–4.22(m, 1H), 5.06(ABq, 2H), 6.80–7.52(m, 16H) and 9.15(s, 1H).

EXAMPLE-4

(3S,4S)-3-[2S-2-(3-phenylpropionyl)-amino-2-benzyl]-acetamido-3-methyl-4-acetoxy azetidine-2-one

Step-1: Preparation of benzyl-6-amino-penicillinate p-TsOH salt

A suspension of 6-amino penicillanic acid (103.68 g,. 0.4794 mol) in dry chloroform (1.2 L) under nitrogen was treated with triethyl amine (97.02 g, 0.959 mol) at room temperature. The reaction mixture was stirred for 5 hrs, and to the clear solution obtained was added methyl acetoacetate, stirred at room temperature for 16 hrs. and evaporated in vacuo. The gummy mass obtained was dissolved in dry dimethy formamide (350 ml) and benzyl bromide was added drop wise. After stirring for 8 hrs at room temperature was added 1.5 L of ether. The suspension obtained was filtered and the filtrate was washed with water (5×1 L) followed by aq. sat. sodium bicarbonate solution (2×1 L), brine (1 L0, dried over anhyd. magnesium sulfate, filtered and evaporated in vacuo to give a gummy product. The above gummy product was dissolved in ethyl acetate and was added p-toluene sulfonic acid monohydrate in portions. After stirring at room temperature for 2 hrs the resulting suspension was filtered, washed with ether followed by hexanes and air dried to give a white solid (136.56 g).

Yield: 92.25%.

Step 2: Preparation of benzyl-6-(benzylidene)-imino-penicillinate

A suspension of benzyl-6-amino penicillin p-toluene sulfonate (118 g, 0.2466 mol) in ethyl acetate (1 L) was treated with aq. sat. NaHCO$_3$ (1 L) and stirred at room temperature for 1 hr. The organic layer was separated, washed brine solution (600 ml), dried over anhyd. magnesium sulfate, filtered and concentrated to 800 ml.

To the ethyl acetate solution was added anhydrous magnesium sulfate (200 g) followed by banzaldehyde (28.141 g, 0.2652 mol) and the resulting suspension was stirred under nitrogen at room temperature for 16 hrs. The suspension was filtered, washed with aq. sodium bisulfite (10%, 2×500 ml)) followed by aq.sat.sodium bicarbonate (600 ml), brine solution (600 ml) and dried over magnesium sulfate. Filtration followed by evaporation of the solvent in vacuo gave the desired product semi solid (92 g)

Yield: 96.8%

$^1$H NMR (DMSO-d$_6$): δ1.38 and 1.58(2s, 6H), 4.42(s, 1H), 5.22(ABq, 2H, J=1.4 Hz and 12.3 Hz), 5.57(dd, 1H, J=2.58 and 1.6 Hz), 5.67(d, 1H, J=4.3 Hz), 7.30–7.80(m, 10H) and 8.55(d, 1H, J=1.6 Hz).

Step 3: Preparation of benzyl-6-amino-6-methyl-penicillin p-TsOH salt

A solution of benzyl 6-(benzylidene)-imino-penicillanate (72.7 g, 184.33 mmol) in dry dimethoxy ethane (375 ml) under nitrogen was cooled to −60° C. To the solution was added potassium tert-butoxide (21.424 g, 190.76 mmol) in portions over 20 min. and the resulting orange-red colored slurry was stirred for 30 min. Then was added methyl iodide (52.33 g, 369.2 mmol) and the reaction mixture was allowed to come to 20° C. over 1 h and quenched with 10 ml water. The reaction mixture was diluted with ethyl acetate (1.3 LI), washed with water (4×100 ml), brine solution, dried over magnesium sulfate, filtered and evaporated in vacuo to give a gummy product (70.66 g, 93.8%).

The above gummy product was dissolved in ethyl acetate (800 ml) and was added p-toluene sulfonate (36.19 g, 190 mmol) portion resulting in the separation of a solid instantly. After stirring for 2 hrs. at room temperature the suspension was filtered washed sequentially with cold(~6° C.) ethyl acetate, ether followed by hexanes and air dried to give a white solid (56.4 g).

Yield: 66.2%.

$^1$H NMR (DMSO-d$_6$): δ1.38(s, 3H), 1.68 and 1.61(2s, 6H), 2.29(s, 3H), 4.58(s, 1H), 5.23(s, 2H), 5.41(s, 1H), 7.10–7.50(m, 9H), 8.83(br s, 3H).

Step 4. Preparation of benzyl 6-(N-benzyloxycarbonyl)-amino-6-methy-penicillanate Benzyl-6-amino-6-methyl-penicillin p-TsOH salt (22.1 g, 44.862 mol)was suspended in a mixture of ethyl acetate (250 ml) and dd. Water (170 ml) and was treated with sodium bicarbonate(s) over 10 min. After stirring for 15 min., the mixture was treated with benzyloxy carbonyl chloride and stirred vigorously at room temperature for 2.5 hrs. The resulting mixture was diluted with brine solution (150 ml), ethyl acetate (100 ml) and the organic layer was separated. The ethyl acetate solution was washed sequentially with aq. sat. NaHCO$_3$, water, 1N. HCl, water, brine, dried over sodium sulfate and filtered. Evaporation of the solvent in vacuo resulted in the desired product as a sticky oil (20.2 g)

Step 5: Synthesis of N-[(2-carboxybenzyl-1-propylidene) 1-yl]3-(benzyloxycarbonyl)-amino-3-methyl-4-(R)-phenoxy-azetidine-2-one A solution of benzyl 6-(N-benzyloxy carbonyl)-amino-6-methy-penicillanate (7.14 g, 15.71 mmol) in glacial acetic acid (35 ml) was treated with mercuric acetate(10.01 g, 31.42 mmol). The suspension was then stirred at 75° C. for 1.15 h and cooled to room temperature. The slurry was filtered and the filtrate was concentrated in vacuo. The residue obtained was diluted with ethyl acetate (200 ml), washed with cold water (2×200 ml), aq. sat. NaHCO$_3$ (2×200 ml), water, brine solution and dried over sodium sulfate. Filtration followed by evaporation of the solvents in vacuo gave an oil (6.67 g, 88.3%), which upon purification over a silica gel column gave the desired compound (2.4 g), as a sticky oil.

Yield: 31.8%.

$^1$H NMR (DMSO-d$_6$): δ1.19(3s, 3H), 1.99(s, 6H), 2.15(s, 3H), 5.03(s, 2H), 5.15(d, 2H, J=2.0 Hz), 6.30(s, 1H), 7.31–7.77(m, 10H), 8.05(s, 1H).

Step-6: (3S,4S)-3-(N-benzyloxycarbonyl)-amino-3-methyl-4-acetoxy azetidine-2-one The starting material (15.84 g, 32.97 mmol) from step-5 was dissolved in a mixture of acetone (60 ml), acetic acid (35 ml) and water (75 ml ) and was cooled to ~5° C. in an ice-water bath. To the above reaction mixture was added solid KMnO$_4$ (7.82 g, 49.46 mmol) in portions and the resulting solution was stirred for 45 min. at ~5° C., then diluted with ethyl acetate (250 ml). The reaction was quenched with hydrogen peroxide (~30%) solution and the organic layer was separated. The aqueous layer was reextracted with ethyl acetate and the combined organic extracts were pooled together, washed with aq. sat. NaHCO$_3$ (3×200 ml), water, brine and dried over magnesium sulfate. Filtration followed by evaporation of the solvent in vacuo gave a sticky foam, which was purified over silica gel column (hexane:EtOAc/1:1) to give the title compound as solid(6.3 g).

Yield: 47.8%; m.p.: 150–151° C.

$^1$H NMR (DMSO-d$_6$): δ1.24(s, 3H), 2.09(s, 3H), 5.04(s, 2H), 5.96(s, 1H), 7.37(s, 3H), 7.91(s, 1H) and 8.98(s, 1H).

Step-7: (3S,4S)-3-[2S-2-(3-phenylpropionyl)-amino-2-benzyl]-acetamido-3-methyl-4-acetoxy azetidine-2-one A solution of (3S,4S)-3-(N-benzyloxycarbonyl)-amino-3-methyl-4-acetoxy azetidine-2-one (0.35 g, 1.1974 mmol) in dry THF (30 ml) was hydrogenated in presence of 10%Pd-C(50% wet, 0.35 g) at 344,737.85 N/m$^2$ (50 psi) over 2 hrs. The resulting mixture was filtered through Celite in to a solution of benzotriazolyl-N-(3-phenylpropionyl)amido phenyl alanine in dry THF, which is prepared by the reaction of N-(3-phenylpropionyl)amino phenyl alanine (0.356 g, 1.1974 mol) in (30 ml), with DCC (0.247 g, 1.1974 mmol) and 1-HBT (0.162 g, 1.1974 mmol) at 10° C. and stirring for 1 hr. The reaction mixture was stirred at room temperature for 1 hr. and evaporated in vacuo to give the crude product. The above crude compound was purified over silica gel column, using a mixture of hexane:ethyl acetate(3:2) to give (3S,4S)-3-[2S-2-(3-phenylpropionyl)amino-2-benzyl]-acetamido-3-methyl-4-acetoxy azetidine-2-one (0.32 g).

Yield: 61.1%; m.p.: 92–93° C.

$^1$H NMR (DMSO-d$_6$): δ1.26 (s, 3H), 2.10 (s, 3H), 2.32–3.00(m, 6H), 4.60–4.71(m, 1H), 5.85(s, 1H), 7.10–7.28(m, 10H), 8.10(d, 1H, J=8.5 Hz), 8.43 (s, 1H), 9.00(s, 1H).

EXAMPLE-5

(3S,4S)-3-[2S-2-(3-phenylpropionyl)-amino-2-benzyl]-acetamido-3-methyl-4-phenoxy azetidine-2-one.

Step-1: (3S,4SR)-3-(N-benzyloxycarbonyl)-amino-3-methy4-phenoxy azetidin-2-ones: A solution of (3S,4S)-3-(N-benzyloxycarbonyl)-amino-3-methyl-4-acetoxy azetidine-2-one (3.383 g, 11.574 mmol) in a mixture of tetrahydrofuran(40 ml) and water(10 ml) was cooled to 0° C. and treated with an aqueous NaOH(0.509 g, 15 ml of water)solution of phenol(1.31 g, 13.89 mmol)drop wise over 10 min. The resulting solution was stirred at 0° C. for 1 h., at room temperature for 2 hrs., and diluted with ethyl acetate(150 ml) and water(10 ml). The aqueous layer was separated and the organic layer was washed with brine dried over sodium sulfate and filtered. Evaporation of the solvent in vacuo gave a gummy foam, which on purification over silica gel column (hexanes:ethyl acetate/2:3) resulted in the isolation of two diasteriomers.

a). (3S,4S)-3-(N-benzyloxycarbonyl)-amino-3-methy-4-phenoxy azetidin-2-one (1.53 g)

Yield: 40.5%; m.p.:64–65° C.

$^1$H NMR (DMSO-d6): δ1.30(s, 3H), 5.07(s, 2H), 5.66(s, 1H), 6.87–7.38(m, 10H), 8.05(s, 1H) and 9.14(s, 1H).

b). (3S,4R)-3-(N-benzyloxycarbonyl)-amino-3-methy-4-phenoxy azetidin-2-one (1.37 g)

Yield: 36%; m.p.: 69–71° C.

$^1$H NMR (DMSO-d$_6$): δ1.46(s, 3H), 5.01(ABq, 2H, J=19.0 Hz and 12.8 Hz), 5.45(s, 1H), 6.75–7.33(m, 10H), 7.64(s, 1H) and 9.00(s, 1H).

Step 2: (3S,4S)-3-[2S-2-(3-phenylpropionyl)-amino-2-benzyl]-acetamido-3-methyl-4-acetoxy azetidine-2-one A solution of (3S,4S)-3-(N-benzyloxycarbonyl)-amino-3-methy-4-phenoxy azetidin-2-one (0.5 g, 1.532 mmol) in dry THF (25 ml) was hydrogenated in presence of 10%Pd-C (50% wet, 0.5 g) at 344,737.85 N/m$^2$ (50 psi) over 3 hrs. The resulting mixture was filtered through Celite in to a solution of benzotriazolyl-N-(3-phenyl propionyl)-amino phenyl alanine in dry THF, which is prepared by the reaction of N-(3-phenylpropionyl)-amino phenyl alanine (0.456 g, 1.532 mmol) in THF (20 ml), with DCC (0.316 g, 1.532 mmol) and 1-HBT (0.207 g, 1.532 mmol) at 10° C. and stirring for 1 hr. The reaction mixture was stirred at room temperature for 1 hr. and evaporated in vacuo to give the crude product. The above crude compound was purified over silica gel column, using a mixture of hexane:ethyl acetate (3:2 to 2:3) to give (3S, 4S)-3-[2S-2-(3-phenylpropionyl)-amino-2-benzyl]-acetamido-3-methyl-4-acetoxy azetidine-2-one (0.51 g).

Yield: 70.5%; m.p.: 163–164° C.

$^1$H NMR (DMSO-d$_6$): δ1.29(s, 3H), 2.34–2.94(m, 6H), 4.65–4.75(m, 1H), 5.51(s, 1H), 6.79–7.35(m, 15H), 8.18(d, 1H, J=8.5 Hz), 8.54(s, 1H) and 9.14(s, 1H).

EXAMPLE-6

(3S, 4R)-3-[2S-2(3-phenylpropionyl)amino2-benzyl]-acetamido-3-methyl-4-acetoxy azetidine-2-one A solution of (3S,4R)-3-(N-benzyloxycarbonyl)-amino-3-methy-4-phenoxy azetidin-2-one (0.52 g, 1.5934 mmol) in dry THF (30 ml) was hydrogenated in presence of 10%Pd-C (50% wet, 0.5 g) at 344,737.85 N/m$^2$ (50 psi) over 4 hrs. The resulting mixture was filtered through Celite in to a solution of benzotriazolyl-N-(3-phenylpropionyl)-amino phenyl alanine in dry THF, which is prepared by the reaction of N-(3-phenylpropionyl)-amino phenyl alanine (0.474 g, 1.5934 mmol) in THF (20 ml), with DCC (0.329 g, 1.5934 mmol) and 1-HBT (0.215 g, 1.5934 mmol) at 10° C. and stirring for 1 hr. The reaction mixture was stirred at room temperature for 2 hr. and evaporated in vacuo to give the crude product. The above crude compound was purified over silica gel column, using a mixture of hexane:ethyl acetate (1:1 to 3:7) to give (3S,4R)-3-[2S-2-(3-phenylpropionyl)-amino-2-benzyl]-acetamido-3-methyl-4-acetoxy azetidine-2-one (0.5.6 g)

Yield: 74.6%.; m.p.:204–206° C.

$^1$H NMR (DMSO-d$_6$): δ1.54(s, 3H), 2.24–2.66(m, 6H), 4.50–4.63(m, 1H), 5.46(s, 1H), 6.81–7.34(m, 15H), 8.16(d, 1H, J=8.9 Hz), 8.27(s, 1H) and 9.04(s, 1H).

EXAMPLE-7

(3S,4S)-3-[2S-2-(6-N, N-dibenzyloxycarbonylguanidino hexanoyl)-amino-2-cyclohexylmethyl]-acetamido-3-methyl-4-phenoxy-azetidine-2-one A solution of (3S,4S)-3-(N-benzyloxycarbonyl)-amino-3-methy-4-phenoxy azetidin-2-one (0.425 g, 1.3023 mmol) in dry THF (20 ml) was hydrogenated in presence of 10%Pd-C(50% wet, 0.4 g) at 344,737.85 N/m$^2$ (50 psi) over 2 hrs. The resulting suspension was filtered through Celite in to a pre-filtered solution of benzotriazolyl-2-[6-(N,N-dibenzyloxycarbonylguanidino hexanoyl)-amino-2-cyclohexylmethyl]-acetate, prepared by reacting 2-[6-(N,N-dibenzyloxycarbonyl-guanidinohexanoyl)-amino-2-cyclohexylmethyl]-acetic acid (0.775 g, 1.3023 mmol) in dry THF (20 ml) with DCC (0.269 g, 1.3023 mmol) and 1-HBT (0.176 g, 1.3023 mmol) under nitrogen at 10° C. and stirring for 2 hrs. The reaction mixture was stirred at room temperature for 2 hrs. and evaporated in vacuo to give the crude product. Purification of the above crude product over silica gel column, using a gradient mixture of hexane:ethyl acetate(1:1 to 3:7) gave the title compound (0.388 g).

Yield: 38.8%, m.p.: 76–77° C.

$^1$H NMR (DMSO-d$_6$): δ0.80–1.70(m, 22H), 2.10–2.20(m, 2H), 3.25–3.35(m, 2H), 4.40–4.50(m, 1H), 5.03(s, 2H), 5.21(s, 2H), 5.61(s, 1H), 6.85–7.41(m, 15H), 7.95(d, 1H, J=9.0 Hz), 8.40(s, 2H), 9.10(s, 1H), 1.60(s, 1H).

EXAMPLE-8

(3S,4R)-3-[2S-2-(tert-butoxycarbonyl)-amino-2-cyclohexylmethyl]-acetamido-3-methyl-4-phenoxy-azetidine-2-one A solution of (3S,4R)-3-(N-benzyloxycarbonyl)-amino-3-methy-4-phenoxy azetidin-2-one (0.775 g, 2.3748 mmol)

in dry THF (25 ml) was hydrogenated in presence of 10%Pd-C (50% wet, 0.77 g) at 344,737.85 N/m$^2$ (50 psi) over 2.5 hrs. The resulting suspension was filtered through Celite in to a pre-filtered solution of benzotriazolyl-2-(N-tert-butoxycarbonyl)-amino-2-cyclohexyl methyl acetate, prepared by reacting 2-(N-tert-butoxycarbonyl)-amino-2-cyclohexyl methyl acetic acid (0.651 g, 2.3748 mmol) in dry THF (25 ml) with DCC (0.515 g, 2.3748 mmol) and 1-HBT (0.337 g, 2.3748 mmol) under nitrogen at 10° C. and stirring for 1 hr. The reaction mixture was stirred at room temperature for 2 hrs., and evaporated in vacuo. The crude product thus obtained was purified over silica gel column using a gradient mixture of hexane:ethyl acetate (1:1 to 3:7) to give the title compound (0.52 g) as a white foam.

Yield: 66.2%; m.p.: 107–108° C.

$^1$H NMR (DMSO-d$_6$): δ0.60–1.70(m, 25H), 3.96–4.12(m, 1H), 5.39(s, 1H), 6.67–7.32(m, 6H), 7.95(s, 1H) and 8.98(s, 1H).

EXAMPLE-9

(3S,4R)-3-[2S-2-(6-N,N-dibenzyloxycarbonylguanidino hexanoyl)-amino-2-cyclohexylmethyl]-acetamido-3-methyl-4-phenoxy azetidine-2-one Step-1: (3S,4R)-3-(S-2-amino-2-cyclohexylmethyl)-acetamido-3-methyl-4-phenoxy-azetidine-2-one trifluoro acetic acid salt A solution of (3S,4R)-3-[2S-2-(tert-butoxycarbonyl)-amino-2-cyclohexylmethyl]-acetamido-3-methyl-4-phenoxy azetidine-2-one (0.51 g, 1.15 mmol) in dry methylene chloride (10 ml) under nitrogen was cooled to 0° C. and treated with trifluoro acetic acid (4 ml). The resulting solution was stirred between 15 to 20° C. for 1 hr and evaporated in vacuo. The crude product obtained was further triturated with ether, then with hexanes, filtered and dried to give a white solid (0.464 g).

Yield: 88.2%

Step-2: (3S,4R)-3-[2S-2-(6-N,N-dibenzyloxycarbonylguanidino hexanoyl)-amino-2-cyclohexylmethyl]-acetamido-3-methyl-4-phenoxy-azetidine-2-one A mixture of 6-(N,N-dibenzyloxycarbonyl)-guanidino hexanoic acid (0.446 g, 1.01 mmol), DCC (0.208 g, 1.01 mmol) and 1-HBT (0.137 g, 1.01 mmol) in dry THF (35 ml) was stirred under nitrogen, at room temperature for 1.5 hrs. The resulting suspension was cooled to 0° C. and filtered in to (3S,4R)-3-(2S-2-amino-2-cyclohexylmethyl)-acetamido-3-methyl-4-phenoxy-azetidine-2-one trifluoro acetic acid salt (0.464 g, 1.10 mmol) in dry THF (15 ml) The reaction mixture was treated with triethyl amine (0.112 g, 1.11 mmol), stirred for 2 hrs., at room temperature and diluted with ethyl acetate (80 ml). The EtOAc solution was washed with water, aq. sat. NaHCO$_3$ (2×80 ml), brine solution, dried over magnesium sulfate and filtered. Evaporation of the solvent in vacuo gave the crude material which was purified by silica gel column using a mixture of hexane:ethyl acetate (3:7)to give the title compound (0.22 g).

Yield: 28.3%; m.p.: 108–109° C.

$^1$H NMR (DMSO-d$_6$): δ0.58–1.63(m, 22H), 2.00–2.20(m, 2H), 3.25–3.35(m, 2H), 4.33–4.42(m, 1H), 5.03(s, 2H), 5.21(s, 2H), 5.38(s, 1H), 6.76–7.41(m, 15H), 7.83(d, 1H, J=9.0 Hz), 8.00(s, 1H), 8.39(t, 1H, J=3.0 Hz), 8.96(s, 1H), 11.60(s, 1H).

EXAMPLE-10

(3S,4S)-3-[2S-2-(6-N,N-di-tert-butoxycarbonylguanidino hexanoyl)-amino-2-cyclohexylmethyl]-acetamido-3-methyl-4-phenoxy-azetidine-2-one A solution of (3S,4S)-3-(N-benzyloxycarbonyl)-amino-3-methy-4-phenoxy azetidin-2-one (0.714 g, 2.188 mmol) in dry THF (28ml) was hydrogenated in presence of 10%Pd-C (50% wet, 0.720) at 344,737.85 N/m$^2$ (50 psi) over 2.5 hrs. The resulting suspension was filtered through Celite in to a pre-filtered solution of benzotriazolyl-2-[6-(N,N-di-tert-butoxycarbonylguanidino hexanoyl)-amino-2-cyclohexyl methyl]-acetate, prepared by reacting a mixture of 2-[6-(N,N-di-tert-butoxycarbonyl guanidino hexanoyl)-amino-2-cyclohexyl methyl]-acetic acid (1.21 g, 2.297 mmol), DCC (0.474 g, 2.297 mmol) and 1-HBT (0.310 g, 2.297 mmol) in dry THF (30 ml), at room temperature and stirring for 1.5 hrs. The resulting reaction mixture was stirred at room temperature for 2 hrs. and evaporated in vacuo. The crude product thus obtained was purified over silica gel column using a mixture of hexanes: ethyl acetate (3:7) to give the title compound (0.68 g).

Yield: 44.4%; m.p. :119–121° C.

$^1$H NMR (DMSO-d$_6$): δ0.80–1.75(m, 40H), 2.10–2.20(m, 2H), 3.20–3.30(m, 2H,), 4.40–4.50(m, 1H), 5.61(s, 1H), 6.85–7.35(m, 5H), 7.93(d, 1H, J=5.0 Hz), 8.25(t, 1H, J=3.0 Hz,), 8.27(s, 1H), 9.10(s, 1H), 11.51(s, 1H).

EXAMPLE-11

(3S,4R)-3-[2S-2-(N-benzyloxycarbonyl)-amino-2-benzyl]-acetamido-3-methyl-4-phenoxy azetidin-2-one A solution of (3S,4R)-3-(N-benzyloxycarbonyl)-amino-3-methy-4-phenoxy azetidin-2-one (0.35 g, 0.92 mmol) in ethyl acetate (20 ml) was hydrogenated in presence of 10%Pd-C (50% wet, 0.3 g) at 344,737.85 N/m$^2$ (50 psi) over 1.5 hrs. The resulting mixture was filtered through Celite in to a solution of benzotriazolyl-2-(N-benzyloxycarbonyl)-amino-3-phenylpropionate(CbzPhe) in dry THF, which is prepared by the reaction of N-(benzyloxycarbonyl)amino-phenylalanine (0.275 g, 0.92 mmol) in THF (6 ml), with DCC (0.190 g, 0.92 mmol) and 1-HBT (0.124 g, 0.92 mmol) at 10° C. and stirring for 1.5 hrs., followed by filtration. The reaction mixture was stirred at room temperature for 2 hrs., washed with aq. sat. sodium bicarbonate, followed by water, brine and dried over anhyd. sodium sulfate. Filtration followed by evaporation of the solvent in vacuo afforded the crude product, which was purified by silica gel column chromatography using a gradient mixture of ethyl acetate and hexanes (1:1 to 1:0) to give the title compound (0.160 g).

Yield: 37%; m.p.: 103–105° C.

$^1$H NMR (DMSO-d$_6$): δ1.55(s, 3H), 2.55–2.70(m, 2H), 4.23–4.34(m, 1H), 4.91(s, 2H), 5.46(s, 1H), 6.81–7.80(m, 15H), 7.55(d, 1H, J=1.5 Hz), 8.27(s, 1H), 9.05(s, 1H).

EXAMPLE-12

(3S,4S)-3-[2S-2-(N-tert-butoxycarbonyl)-amino-2-(Pyridin-3-yl)]-acetamido-3-methyl-4-phenoxy azetidin-2-one A solution of (3S,4S)-3-(N-benzyloxycarbonyl)-amino-3-methy-4-phenoxy azetidin-2-one (0.3 g, 0.92 mmol) in dry THF (30 ml) was hydrogenated in presence of 10%Pd-C (50% wet, 0.3 g) at 344,737.85 N/m² (50 psi) over 2 hrs. The resulting mixture was filtered through Celite in to a solution of benzotriazolyl-2-(N-tert-butoxycarbonyl)-amino-2-(pyridin-3-yl)-acetate in dry THF, which is prepared by the reaction of 2-(N-tert-butoxycarbonyl)-amino-2-(pyridin-3-yl)-acetic acid (0.245 g, 0.92 mmol) in THF (20 ml), with DCC (0.190 g, 0.92 mmol) and 1-HBT (0.124 g, 0.92 mmol) at 10° C. and stirring for 2 hrs., followed by filtration. The reaction mixture was stirred at room temperature for 2 hrs., and evaporated in vacuo. The crude product obtained was purified by silica gel column chromatography using a gradient mixture of ethyl acetate and methanol (9.5:0.5) to give the desired (3S,4S)-3-[2S-2-(N-tert-butoxycarbonyl)-amino-2-(pyridin-3-yl)]-acetamido-3-methyl-4-phenoxy azetidin-2-one (0.35 g).

Yield: 86.4%; m.p.: 109–110° C.

¹H NMR (DMSO-d₆): δ1.29(s, 9H), 1.33(s, 3H), 2.75–3.05(m, 2H), 4.26–4.40(m, 1H), 5.57(s, 1), 6.83–7.37 (m, 7H), 7.68(d, 1H, J=7.9 Hz), 8.38(d, 1H, J=4.6 Hz), 8.48 and 8.52(2s, 2H), 9.17(s, 1H).

EXAMPLE-13

(3S,4S)-3-[2S-2-(N-benzyloxycarbonyl)-amino-2-(pyridin-3-yl)]-acetamido-3-methyl-4-phenoxy azetidin-2-one Step 1: (3S,4S)-3-[2S-2-amino-2-(pyridin-3-yl)]-acetamido-3-methyl-4-phenoxy azetidin-2-one trifluoroacetate salt A solution of (3S,4S)-3-[2S-2-(N-tert-butoxycarbonyl)-amino-2-(pyridin-3-yl)]-acetamido-3-methyl-4-phenoxy azetidin-2-one (0.300 g, 0.681 mmol) in dry methylene chloride (8 ml) under nitrogen was cooled to 0° C. Then was added trifluoro acetic acid (6 ml) and the reaction mixture was stirred at 0° C. for 2 hrs and at room temperature for 1 hr. The volatile solvents were evaporated in vacuo and the gum thus obtained was triturated with ether. The solid obtained was filtered and dried to give (3S,4S)-3-[2S-2-amino-2-(pyridin-3-yl)]-acetamido-3-methyl-4-phenoxy azetidin-2-one trifluoroacetate salt (0.294 g, 76%) as a solid.

¹H NMR (DMSO-d₆): δ1.33(s, 3H), 3.12–3.25(m, 2H), 4.14(brs, 1H), 5.51(s, 1H), 6.82–7.46(m, 6H), 7.83(d, 1H, J=7.8 Hz), 8.34(brs, 3H), 8.54–8.60(m, 3H), 9.05(s, 1H), 9.32(s, 1H).

Step2: (3S,4S)-3-[2S-2-(N-benzyloxycarbonyl)-amino-2-(pyridin-3-yl)]-acetamido-3-methyl-4-phenoxy azetidin-2-one A solution of (3S,4S)-3-[2S-2-amino-2-(pyridin-3-yl)]-acetamido-3-methyl-4-phenoxy azetidin-2-one trifluoroacetate salt (0.274 g, 0.482 mmol) in dry THF (30 ml) under nitrogen was cooled to 0° C., and was added triethyl amine (0.122 g, 1.205 mmol). With in 2 min., N-(benzyloxycarbonyl)succinimide (0.132 g, 0.5302 mmol) was added to the reaction mixture and stirred at 0° C. for 1 hr. The solvents were evaporated in vacuo and the crude product was dissolved in ethyl acetate (50 ml). The ethyl acetate solution was washed with aq. sat. sodium bicarbonate, brine solution and dried over anhydr. sodium sulfate. Filtration followed by evaporation of the solvent in vacuo to give a gummy product, which was purified by silica gel chromatography using a mixture of EtOAc:MeOH (9:1) to give the title compound (0.16 g).

Yield: 70%; m.p.: 84–86° C.

¹H NMR (DMSO-d₆): δ1.34(ms, 3H), 2.77–3.10(m, 2H), 4.33–4.50(m, 1H), 4.96(s, 2H), 5.57(s, 1H), 6.82–7.73(m, 13H), 8.40–8.50(m, 2H), 8.60(s, 1H), 9.18(s, 1H).

EXAMPLE-14

(3S,4R)-3-[2S-2-(N-tert-butoxycarbonylamino)-2-(pyridin-3-yl)]-acetamido-3-methyl-4-phenoxy azetidin-2-one A solution of (3S,4R)-3-(N-benzyloxycarbonyl)-amino-3-methy-4-phenoxy azetidin-2-one (0.176 g, 0.54 mmol) in dry THF (20 ml) was hydrogenated in presence of 10%Pd-C (50% wet, 0.176 g) at 344,737.85 N/m² (50 psi) over 2 hrs. The resulting mixture was filtered through Celite in to a solution of benzotriazolyl-2-(N-tert-butoxycarbonyl)-amino-2-(pyridin-3-yl)-acetate in dry THF, which is prepared by the reaction of 2-(N-tert-butoxycarbonyl)-amino-2-(pyridin-3-yl)-acetic acid (0.144 g, 0.54 mmol) in THF (20 ml), with DCC (0.112 g, 0.54 mmol) and 1-HBT (0.073 g, 0.54 mmol) at 10° C. and stirring for 2 hrs., followed by filtration. The reaction mixture was stirred at room temperature for 2 hrs. and evaporated in vacuo. The crude product obtained was purified by silica gel column chromatography using a gradient mixture of ethyl acetate and methanol(9:1) to give the desired (3S,4R)-3-[2S-2-(N-tert-butoxycarbonyl)-amino-2-(pyridin-3-yl)]-acetamido-3-methyl-4-phenoxy azetidin-2-one (0.069 g).

Yield: 29%; m.p.: 94–96° C.

¹H NMR (DMSO-d₆): δ1.29(s, 9H), 1.33(s, 3H), 2.75–3.05(m, 2H), 4.26–4.40(m, 1H), 5.57(s, 1), 6.83–7.37 (m, 7H), 7.68(d, 1H, J=7.9 Hz), 8.38(d, 1H, J=4.6 Hz), 8.58 and 8.52(2s, 2H), 9.17(s, 1H).

EXAMPLE-15

(3S,4S)-3-[2S-2-(N-benzyloxycarbonyl)-amino-2-benzyl]-acetamido-3-methyl-4-acetoxy azetidine-2-one A solution of (3S,4S)-3-(N-benzyloxycarbonyl)-amino-3-methyl-4-acetoxy azetidine-2-one (1.302 g, 4.4544 mmol) in dry THF (35 ml) was hydrogenated in presence of 10%Pd-C(50% wet, 1.30 g) at 45 psi over 2 hrs. The resulting mixture was filtered through Celite in to a solution of benzotriazolyl-2-(N-benzyloxycarbonyl)-amino phenyl alanine in dry THF, which is prepared by the reaction of N(benzyloxycarbonyl)amido phenyl alanine (1.333 g, 4.4544 mmol) in (45 ml), with DCC (0.919 g, 4.4544 mmol) and 1-HBT (0.602 g, 4.4544 mmol) at 10° C. and stirring for 1 hr. The reaction mixture was stirred at room temperature for 1 hr. and evaporated in vacuo to give the crude product. The above crude compound was purified over silica gel column, using a mixture of hexane:ethyl acetate(2:3) to give (3S,4S)-3-[2S-2-(N-benzyloxycarbonyl)-amino-2-benzyl]-acetamido-3-methyl-4-acetoxy azetidine-2-one.

Yield: 1.25 g (63.8%); m.p.: 86–88° C.

¹H NMR (DMSO-d₆): δ1.28(s, 3H), 2.10(s, 3H), 2.70–3.00(m, 2H), 4.30–4.40(m, 1H), 4.94(ABq, 2H, J=2.0 Hz), 5.87(s, 1H), 7.22–7.34(m, 10H), 7.50(d, 1H), 8.45(s, 1H), 9.01(s, 1H).

EXAMPLE-16

(3S,4S)-3-[2S-2-(N-benzyloxycarbonyl)-amino-2-benzyl]-acetamido-3-methyl-4-(benzothiazol-2-yl)-mercapto azetidine-2-one (16A) and (3S,4R)-3-[2S-2-(N-benzyloxycarbonyl)-amino-2-benzyl]-acetamido-3-methy-4-(benzothiazol-2-yl)-mercapto azetidin-2-one (16B)

A solution of (3S,4S)-3-[2S-2-(N-benzyloxycarbonyl)-amino-2-benzyl]-acetamido-3-methyl-4-acetoxy azetidine- 2-one (0.286 g, 0.651 mmol) in a mixture of tetrahydrofuran (20 ml) and water(5 ml) was cooled to 0° C. and treated with an aqueous NaOH(0.029 g, 0.716 mol in 15 ml of water) solution of 2-mercaptobenzothiazole(0.131 mg, 0.781 mmol) drop wise over 10 min. The resulting solution after stirring at 0° C. for 1 h. and at room temperature for 3 hr. was diluted with ethyl acetate(100 ml) and brine solution(20 ml). The aqueous layer was separated and the organic layer was washed with brine dried over anhydrous magnesium sulfate and filtered. Evaporation of the solvent in vacuo gave a gummy foam, which on purification over silica gel column (hexanes:ethyl acetate/2:3) resulted in the isolation of two diasteriomers.

a). (3S,4S)-3-[2S-2-(N-benzyloxycarbonyl)-amino-2-benzyl]-acetamido-3-methyl-4-(benzothiazol-2-yl)-mercapto azetidine-2-one (0.028 g)

Yield: 8%; m.p.: 83–85° C.

$^1$H NMR (DMSO-d6): δ1.43(s, 3H), 2.75–3.10(m, 2H), 4.35 4.45(m, 1H), 4.96(ABq, 2H, J=2.8 Hz), 5.92(s, 1H), 7.15–7.50(m, 12H), 7.58(d, 1H, J=8.7 Hz), 7.87(d, 1H, J=7.0 Hz), 8.05(d, 1H, J=7.0 Hz), 8.61(s, 1H), 9.13(s, 1H).

b). (3S,4R)-3-(N-benzyloxycarbonyl)-amino-2-benzyl]-acetamido-3-methy-4-(benzothiazol-2-yl)-mercapto azetidin-2-one (0.03 g)

Yield: 8.4%; m.p.: 108–110° C.

$^1$H NMR (DMSO-d$_6$): δ1.21(s, 3H), 2.71–3.24(m, 2H), 4.36–4.52(m, 1H), 4.95(ABq, 2H, J=8.9 Hz), 5.77(s, 1H), 7.03–8.10(m, 15H), 8.70(s, 1H), 9.33(s, 1H).

EXAMPLE-17

(3S,4S)-3-[2S-2-(N-benzyloxycarbonyl)-amino-2-benzyl]-acetamido-3-methyl-4-(3-diphenylmethoxycarbonyl)-phenoxy azetidine-2-ones Stem 1: (3S,4S and 3S,4R)-3-(N-benzyloxycarbonyl)-amino-3-methyl-4-(3-diphenylmethoxycarbonyl)-phenoxy azetidine-2-ones A solution of (3S,4S)-3-(N-benzyloxycarbonyl)-amino-3-methyl-4-acetoxy azetidine-2-one (2.0 g, 6.8 mmol) in THF (15 mml) was added drop wise to a stirred and cooled (0° C.) solution of 3-(diphenylmethoxycarbonyl)-phenol (3.1 g, 10.2 mmol) in a mixture of THF (30 ml) and 1 N. NaOH (8.7 ml). The reaction mixture was stirred at 0° C. for 1 hr., then at room temperature for 2 hrs., and was diluted with ethyl acetate (250 ml) and water (50 ml). The organic layer was separated, washed with water followed by brine solution, dried over anhydr. sodium sulfate, filtered and evaporated in vacuo to give the crude product as a gummy mass. Purification of the above gummy crude product over silica gel column chromatography using a gradient mixture of hexane:ethyl acetate (3:1 to 1:1) gave two diastereomers.

a): (3S,4S)-3-(N-benzyloxycarbonyl)-amino-3-methyl-4-(3-diphenylmethoxycarbonyl)-phenoxy azetidine-2-one $^1$H NMR (DMSO-d$_6$): δ1.31(s, 3H), 5.06(s, 2H), 5.78(s, 1H), 7.05(s, 1H), 7.21–7.59(m, 18H), 7.82(1H, d, J=7.8Hz), 8.07(s, 1H), 9.22(s, 1H).

Yield: 0.9 g (25%)

b): (3S,4R)-3-(N-benzyloxycarbonyl)-amino-3-methyl-4-(3- diphenylmethoxycarbonyl)-phenoxyl azetidine-2-one $^1$H NMR (DMSO-d$_6$): δ1.50(s, 3H), 4.98(ABq, 2H, J=21.6 and 12.0 Hz), 5.61(s, 1H), 7.05–7.95 (m, 21H), 9.06(s, 1H).

Yield: 0.88 g (24%)

Step 2: (3S,4S)-3-amino-3-methyl-4-(3-carboxy)-phenoxy azetidine-2-one

A solution of (3S,4S)-3-(N-benzyloxycarbonyl)-amino-3-methyl-4-(3-diphenylmethanecarboxy)-phenoxy azetidine-2-one (0.9 g, 1.68 mmol) in ethyl acetate (20 ml) was hydrogenated at 344,737.85 N/m$^2$ (50 psi), in presence of 10% Pd-C over 1.5 hrs. The suspension was filtered through Celite and washed with ethyl acetate. The Celite bed was washed with a mixture of acetonitrile:water (1:1, 300 ml), and the acetonitrile:water washings were concentrated to 60 ml, then lyophilized to give the amine as a white solid (0.23 g, 58%).

$^1$H NMR (DMSO-d$_6$): δ1.17(s, 3H), 5.29(s, 1H), 7.21–7.63(m, 4H), 8.92(s, 1H).

Step 3: (3S,4S)-3-amino-3-methyl-4-(3-diphenylmethoxycarbonyl)-phenoxy azetidine-2-one (3S,4S)-3-amino-3-methyl-4-(3-carboxy)-phenoxy azetidine-2-one, obtained from step-2 was dissolved in acetone (30 ml) and was added diphenyl diazomethane (0.19 g, 0.97 mmol) in acetone (10 ml). After stirring over night, the volatiles were evaporated and the crude product obtained was purified by silica gel column chromatography using a gradient mixture of hexanes:ethyl acetate (2:1 to 0:1) to give the desired compound (0.22 g).

Yield: 56%; m.p.: 142–144° C.

$^1$H NMR (DMSO-d$_6$): δ1.16(s, 3H), 2.56(s, 2H), 5.31 (s, 1H), 7.03(s, 1H), 7.35–7.59(m, 12H), 7.74(s, 1H), 8.93(s, 1H).

Step 3: (3S,4S)-3-[2S-2-(N-benzyloxycarbonyl)-amino-2-benzyl]-acetamido-3-methyl-4-(3-diphenylmethoxycarbonyl)phenyl azetidine-2-ones A solution of (3S,4S)-3-amino-3-methyl-4-(3-diphenylmethanecarboxy)phenyl azetidine-2-one (0.060 g, 0.15 mol) in THF (3 ml) was treated with N-(benzyloxycarbonyl)-phenyl alanine (0.045 mg, 0.15 mmol), DCC (0.031 g, 0.15 mmol) and 1-HBT (0.020 g, 0.15 mmol). The mixture was stirred at room temperature for 2 hrs. and was diluted with ethyl acetate. The ethyl acetate solution was washed with aq. sat. sodium bicarbonate solution followed by water and evaporated in vacuo. The crude product obtained was treated with ether and the solid obtained was filtered and dried give the title compound (0.050 g).

Yield: 49%; m.p.: 91–96° C.

$^1$H NMR (DMSO-d$_6$): δ1.33(s, 3H), 2.75–3.12(m, 2H), 4.33–4.48(m, 1H), 4.95(ABq, 2H, J=3.0 Hz), 5.64(s, 1H), 7.01(s, 1H), 7.13–7.60(m, 24H), 7.83(d, 1H, j+7.8 Hz), 8.60s, 1H), 9.24(s, 1H).

EXAMPLE-18

(3S,4S)-3-[2S-2-(3-phenylpropionyl)-amino-2-benzyl]-acetamido-3-methyl-4-(3-diphenylmethoxycarbonyl)-phenoxy azetidine-2-one A solution of (3S,4S)-3-amino-3-methyl-4-(3-diphenylmethoxycarbonyl)-phenoxy azetidine-2-one (0.060 g, 0.15 mmol) in dry THF (3 ml) was treated with N-(3-phenylpropionyl)-amino phenyl alanine (0.44 g, 0.15 mmol), DCC (0.031 g, 0.15 mmol) and 1-HBT (0.020 g, 0.15 mmol). The reaction mixture was stirred at room temperature for 2 hrs. and diluted with ethyl acetate (50 ml).

The ethyl acetate solution was washed with aq. sat. sodium bicarbonate solution followed by water and evaporated in vacuo. The crude product obtained was treated with ether and the solid obtained was filtered and dried to give the title compound (0.070 g).

Yield: 69%; m.p.: 91–95° C.

$^1$H NMR (DMSO-d$_6$): δ1.20(s, 3H), 2.32–2.40(m, 2H), 2.68–3.05(m, 4H), 4.65–4.75(m, 1H), 5.60(s, 1H), 7.05–7.53(m, 24H), 7.86(d, 1H, J=7.8 Hz), 8.18(d, 1H, J=8.7 Hz), 8.60(s, 1H), 9.26(s, 1H).

EXAMPLE-19

(3S,4S)-3-[2S-2-(3-phenylpropionyl)-amino-2-benzyl]-acetamido-3-methyl-4-(3-carboxy)-phenoxy azetidine-2-one To a cooled (0° C.) and stirred solution of (3S,4S)-3-[2S-2-(3-phenylpropionyl)-amino-2-benzyl]-acetamido-3-methyl-4-(3-diphenylmethoxycarbonyl)-phenoxy azetidine-2-one (0.060 g, 0.038 mmol) in dry methylene chloride (2 ml) was added with trifluoro acetic acid (1 ml) and anisole (2 drops). The reaction mixture was stirred at 0° C. for 0.5 hr., and evaporated in vacuo. The crude product obtained was treated with a mixture of ether:hexanes (1:1) to give a solid, which was filtered and dried (?) to give the title compound (0.025 g).

Yield: 55%; m.p.: 120–122° C.

$^1$H NMR (DMSO-d$_6$): δ1.32(s, 3H), 2.35–2.39(m, 2H), 2.65–3.14(m, 4H), 4.67–4.78(m, 1H), 5.62(s, 1H), 7.14–7.65(m, 14H), 8.13(d, 1H, J=8.8 Hz), 8.61(s, 1H), 9.20(s, 1H).

EXAMPLE-20

(3S,4S)-3-{2S-2-[5-[-1-piperazine-4-(pyrimidin-2-yl)-5-oxo-pentanoyl)-amino-2-isopropyl]-acetamido-3-methyl-4-phenoxy azetidine-2-one A solution of (3S,4S)-3-[2S-2-(benzyloxycarbonyl)-amino-2-isopropyl]-acetamido-3-methyl-4-phenoxy azetidin-2-one (0.100 g, 0.227 mmol) in a 1:1 mixture of ethyl acetate and THF (15 ml) was hydrogenated at 344, 737.85 N/m$^2$ (50 psi), over 1.5 hrs., in presence of 10% Pd-C (50% wet). The resulting suspension was filtered through Celite and the filtrate was evaporated in vacuo to give the amine, which was dissolved in DMF (5 ml) and stirred under nitrogen. Glutaric anhydride (0.026 g, 0.227 mmol) was added to the above reaction mixture in one portion and after stirring at room temperature for 1 hr., was added HOBT (0.030 g, 0.227 mmol) followed by DCC (0.047 g, 0.227 mmol). After stirring for 0.5 hrs., the reaction mixture was treated with 4-(pyrimidin-2-yl)piperazine dihydrochloride (0.054 g, 0.227 mmol) followed by triethyl amine ( ). The reaction mixture was stirred at room temperature for 2 hrs., then diluted with ethyl acetate (50 ml) and water (50 ml). The organic layer was separated, washed with water, aq. sat. sodium bicarbonate, brine solution, dried over anhydrous sodium sulfate, filtered and evaporated in vacuo. The crude product obtained was treated with ether and the solid obtained was, filtered and dried to give the title compound (0.01 g).

Yield: 8%; m.p.: 115–120° C.

$^1$H NMR (DMSO-d$_6$): δ0.87(d, 3H, J=6.1 Hz), 0.92(d, 3H, J=6.3 Hz), 1.32(s, 3H), 1.20–2.39(m, 12H), 3.52(brs, 2H), 3.72(brs, 3H), 4.40–4.52(m, 1H), 5.62(s, 1H), 6.64(t, 1H, H=4.7 Hz), 6.85–7.37(m, 5H), 8.00(d, 1H, J=8.0 Hz), 8.37 and 8.39(2s, 2H), 8.46(s, 1H), 9.09(s, 1H).

EXAMPLE-21

(3S,4S)-3-[2S-2-(2R-benzyloxycarbonyl)-aminoB2-phenyl)-acetamido-2-isopropyl]-acetamido-3-methyl-4-phenoxy azetidin-2-one A solution of (3S,4S)-3-[2S-2-(benzyloxycarbonyl)-amino-2-isopropyl]-acetamido-3-methyl-4-phenoxy azetidin-2-one (0.24 g, 0.54 mmol) in THF (15 ml) was hydrogenated at 344,737.85 N/m$^2$ (50 psi), over 1.5 hrs. in presence of 10% Pd-C (50% wet). The resulting suspension was filtered through Celite in to a solution of benzotriazolyl-N-(benzyloxycarbonyl)-D-phenyl glycine in THF (5 ml), prepared by reacting N-benzyloxy carbonyl-D-phenyl glycine (0.155 g, 0.54 mol), DCC (0.112 g, 0.54 mmol) and 1-HBT (0.73 g, 0.54 mmol) in dry THF for 1.5 hr., followed by filtration. The reaction mixture was stirred at room temperature for 2 hrs, diluted with ethyl acetate (80 ml) and the organic layer was separated. The ethyl acetate solution was washed with aq. sat. sodium bicarbonate, brine solution, dried over anhydrous sodium sulfate, filtered and evaporated in vacuo. The solid obtained was treated with ether filtered and dried to give the desired compound (0.200 g).

Yield: 64%; m.p.: 117–120° C.

$^1$H NMR (DMSO-d$_6$): δ0.63(d, 3H, J=6.0 Hz), 0.77(d, 3H, J=6.0 Hz), 0.78–0.95(m, 1H), 1.36(s, 3H), 1.26–1.50(m, 2H), 4.25–4.40(m, 1H), 4.90(ABq, 2H, J=12.5 and 17.2 Hz), 5.33(d, 1H, J=7.6 Hz), 5.63(s, 1H), 6.85–7.50(m, 15H), 8.01(d, 1H, J=7.5 Hz), 8.29(s, 1H), 8.56(d, 1H, J=9.0 Hz), 9.12(s, 1H).

Biological Example

Compounds of the invention were shown to be inhibitors of cathepsins B and/or L and/or K and/or S by testing according to the following assays.

Assay Procedure for Cathepsin K

To 170 μl of enzyme-buffer mixture (r Cathepsin K diluted to give approx. 30 F units/min. Buffer: 100 mM sodium acetate, 5 mM EDTA, 20 mM L-Cysteine, 0.01% Brij , pH 5.5), 10 μl of inhibitor (dissolved in 100% DMSO) was added.

After 10 min of incubation at room temperature 20 μl of 2.7 mM substrate (N-CBZ-Phe-Arg-AMC, dissolved in DMSO) was added to initiate reaction. Reading is followed for 10 min at the Fluoroscan II plate reader (excitation at 380 nm, emission at 460 nm).

A plot of percentage of inhibition vs inhibitor concentration is obtained, and the IC50 is determined using a linear regression calculation (concentration of inhibitor which will give 50% inhibition).

Assay Procedure for Cathepsin S

To 170 μl of enzyme-buffer mixture (r Cathepsin S diluted to give approx. 30 F unis/min, buffer: 100 mM sodium phosphate, 1 mM EDTA, 5 mM DTT ,0.01% Brij, pH 6.5.), 10 μl of inhibitor (dissolved in 100% DMSO) was added.

After 10 min of incubation at room temperature 20 μl of 1.2 mM substrate (CBZ-Val-Val-Arg-AMC, dissolved in DMSO) was added to initiate reaction. Reading is followed for 10 min at the Fluoroscan II plate reader (excitation at 380 nm, emission at 460 nm).

A plot of percentage of inhibition vs inhibitor concentration is obtained, and the IC50 is determined using a linear regression calculation (concentration of inhibitor which will give 50% inhibition).

Assay Procedure for Cathepsin B

To 170 µl of enzyme-buffer mixture (r Cathepsin B diluted to give approx. 30 F units/min, buffer: 56 mM Na acetate, 1.124 mM EDTA, 10 mM DTT, pH 5.1), 10 µl of inhibitor (dissolved in 100% DMSO ) was added.

After 10 min of incubation at mom temperature 20 µl of 5 mM substrate (N-CBZ-Phe-Arg-AMC, dissolved in DMSO ) was added to initiate reaction. Reading is followed for 10 min at the Fluoroscan reader (excitation at 380 nm, emission at 460 nm).

A plot of percentage of inhibition vs inhibitor concentration is obtained, and the IC50 is determined using a linear regression calculation (concentration of inhibitor which will give 50% inhibition).

Assay Procedure for Cathepsin L

To 170 µl of an enzyme-buffer mixture (enzyme: r Cathepsin L, diluted to give 25 F units/min, buffer: 58.8 mM Na citrate, 1.18 mM EDTA, 235 mM sodium chloride, 10 mM DTT, pH 5.0), 10 µl of an inhibitor (dissolved in 100% DMSO ) was added.

After 10 min of incubation at room temperature 20 µl of 1 mM substrate (N-CBZ-Phe-Arg-AMC) dissolved in DMSO was added to initiate the reaction. Reading was for 10 min at the Fluoroscan reader (excitation at 380 nm, emission at 460 nm).

A plot of percentage of inhibition vs inhibitor concentration is obtained, and the IC50 is determined using a linear regression calculation (concentration of inhibitor which will give 50% inhibition).

Results: The $IC_{50}$'s for the compounds of Examples 4, 7, 12, 14 and 18 are shown in Table 1. The $IC_{50}$'s of the other compounds of the examples were generally <50 µl M in the case of cathepsin B; <40 µl M in the case of cathepsin L; <40 µl M in the case of cathepsin K; and <10 µM in the case of cathepsin S.

TABLE 1

In vitro inhibitory activity of test compounds (IC50's - µM)

| Example | CatB IC50 | CatL IC50 | CatK IC50 | CatS IC50 |
|---|---|---|---|---|
| 4 | 10.04 | 1.91 | 1.14 | 0.098 |
| 7 | 26.24 | 32.51 | 32.51 | 0.02 |
| 12 | 11.35 | 2.27 | 7.74 | 1.8 |
| 14 | 0.36 | 0.45 | 1.34 | 0.05 |
| 18 | >36.6 | 7.33 | 7.3 | 0.69 |

What is claimed is:

1. A compound of formula (I)

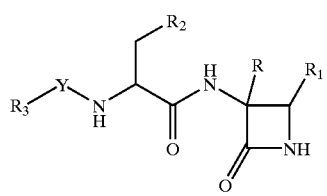

(I)

wherein

Y represents —C(O)— or —S(O₂)—;

R represents an allyl group or a radical of formula $R_4$-(ALK)$_p$-(Z)$_n$-(ALK)$_q$- wherein Z represents —O— or —S—, ALK represents a divalent $C_1$–$C_3$ alkylene or halogen-substituted $C_1$–$C_3$ alkylene radical, $R_4$ represents hydrogen, halogen, phenyl or phenyl substituted with 1, 2, or 3 substituents selected from ($C_1$–$C_3$)alkyl;

phenyl;

hydroxy or mercapto;

($C_1$–$C_3$)alkoxy or ($C_1$–$C_3$)alkylthio;

phenoxy or phenylthio;

halogen;

trifluoromethyl;

nitro;

cyano;

carboxyl or alkoxycarbonyl;

amino, mono- or di-($C_1$–$C_3$)alkylamino, or acylamino;

($C_1$–$C_3$)alkylcarbonyl- or ($C_1$–$C_3$)alkylcarbonyl-amino-;

—CONHR$^A$, NHR$^A$, —NR$^A$R$^B$, or —CONR$^A$R$^B$ wherein R$^A$ and R$^B$ are independently ($C_1$–$C_3$)alkyl; and —NH—C(=NR$_8$)R$_9$ wherein R$_9$ is amino, mono- or di-($C_1$–$C_6$)alkylamino, acylamino, or ($C_1$–$C_3$)alkyl, and R$_8$ is hydrogen, ($C_1$–$C_3$)alkyl or acyl, and n, p and q are independently 0 or 1, PROVIDED THAT (i) when $R_4$ is hydrogen and both p and n are 0 then q is 1; (ii) when $R_4$ is halogen and n is 1 then p is 1; (iii) when $R_4$ is halogen then p, n and q are not all 0; and (iv) when $R_4$ is hydrogen and both q and n are 0 then p is 1;

$R_1$ represents —OCOR$_5$, —OR$_5$, —SR$_5$, —S(O)R$_5$, or —S(O)$_2$R$_5$;

$R_2$ represents a radical of formula $R_6$(ALK)$_p$-(Z)$_n$-(ALK)$_q$- wherein p, Z and ALK are as defined in relation to R, q is 0 or 1, n is 0 or 1 when q is 1 and n is 0 when q is 0, and $R_6$ is hydrogen, $C_1$–$C_6$ alkyl, $C_2$–$C_6$ alkenyl, $C_2$–$C_6$ alkynyl, cycloalkyl, cycloalkenyl, aryl, heterocyclic group, or a $C_1$–$C_6$ alkyl, $C_2$–$C_6$ alkenyl, $C_2$–$C_6$ alkynyl, cycloalkyl, cycloalkenyl, aryl or heterocyclic group substituted with 1, 2, or 3 substituents selected from ($C_1$–$C_3$)alkyl;

phenyl;

hydroxy or mercapto;

($C_1$–$C_3$)alkoxy or ($C_1$–$C_3$)alkylthio;

phenoxy or phenylthio;

halogen;

trifluoromethyl;

nitro;

cyano (—CN);

carboxyl or alkoxycarbonyl;

amino, mono- or di-($C_1$–$C_3$)alkylamino, or acylamino;

($C_1$–$C_3$)alkylcarbonyl- or ($C_1$–$C_3$)alkylcarbonyl-amino-;

—CONHR$^A$, —NHR$^A$, —NR$^A$R$^B$, or —CONR$^A$R$^B$ wherein R$^A$ and R$^B$ are independently ($C_1$–$C_3$)alkyl; and —NH—C(=NR$_8$)R$_9$ wherein R$_9$ is amino, mono- or di-($C_1$–$C_6$)alkylamino, acylamino, or ($C_1$–$C_3$)alkyl, and R$_8$ is hydrogen, ($C_1$–$C_3$)alkyl, or acyl, or R$_2$ together with the carbon atom to which it attaches forms a cycloalkyl ring;

$R_3$ represents —OR$_5$ or —R$_5$;

$R_5$ represents a radical of formula $R_7$—(A)$_t$— wherein t is 0 or 1; A represents (i) a divalent $C_1$–$C_6$ alkylene optionally interrupted by one or more non-adjacent —O—, —S— or —NH— linkages, (ii) a divalent $C_1$–$C_6$ alkylene optionally interrupted by one or more non-adjacent —O—, —S— or —NH— linkages, wherein the alkylene group is substituted with 1, 2, or 3 substituents selected from
(C₁–C₃)alkyl;
phenyl;
hydroxy or mercapto;
(C₁–C₃)alkoxy or (C₁–C₃)alkylthio;
phenoxy or phenylthio;
halogen;
trifluoromethyl;
nitro;
cyano;
carboxyl or alkoxycarbonyl;
amino, mono- or di-(C₁–C₃)alkylamino, or acylamino;
(C₁–C₃)alkylcarbonyl- or (C₁–C₃)alkylcarbonyl-amino-;
—CONHR$^A$, —NHR$^A$, —NR$^A$R$^B$, or —CONR$^A$R$^B$ wherein R$^A$ and R$^B$ are independently (C₁–C₃)alkyl; and
—NH—C(=NR₈)R₉ wherein R₉ is amino, mono- or di-(C₁–C₆)alkylamino, acylamino, or (C₁–C₃)alkyl, and R₈ is hydrogen, (C₁–C₃)alkyl, or acyl;
(iii) a divalent C₂–C₆alkenylene, C₂–C₆alkynylene, cycloalkylene, cycloalkenylene, aryl or heterocyclic radical; or (iv) a —NH— link; and R₇ represents hydrogen, C₁–C₆ alkyl, C₂–C₆ alkenyl, C₂–C₆ alkynyl, cycloalkyl, cycloalkenyl, aryl, heterocyclic group, or a C₁–C₆ alkyl, C₂–C₆ alkenyl, C₂–C₆ alkynyl, cycloalkyl, cycloalkenyl, aryl or heterocyclic group substituted with 1, 2, or 3 substituents selected from
(C₁–C₃)alkyl;
phenyl;
hydroxy or mercapto;
(C₁–C₃)alkoxy or (C₁–C₃)alkylthio;
phenoxy or phenylthio;
halogen;
trifluoromethyl;
nitro;
cyano (—CN);
carboxyl or alkoxycarbonyl;
amino, mono- or di-(C₁–C₃)alkylamino, or acylamino;
(C₁–C₃)alkylcarbonyl- or (C₁–C₃)alkylcarbonyl-amino-;
—CONHR$^A$, —NHR$^A$, —NR$^A$R$^B$, or —CONR$^A$R$^B$ wherein R$^A$ and R$^B$ are independently (C₁–C₃)alkyl; and
—NH—C(=NR₈)R₉ wherein R₉ is amino, mono- or di-(C₁–C₆)alkylamino, acylamino, or (C₁–C₃)alkyl, and R₈ is hydrogen, (C₁–C₃)alkyl, or acyl;
or a pharmaceutically acceptable salt thereof.

2. A compound as claimed in claim 1, wherein Y is —C(O)—.

3. A compound as claimed in claim 1, wherein R is allyl, methyl, ethyl, n-propyl, n-or iso-butyl, methyoxymethyl, ethoxymethyl, benzyl, or phenoxymethyl.

4. A compound as claimed in claim 1, wherein R₁ is acetoxy; butyloxy; 2-carboxyethyloxy; 2-aminoethyloxy; 2-fluoroethoxy; cyclopentyloxy; cyclohexyloxy; cyclohexylthio; phenoxy, phenoxy substituted by methyl, tert-butyl, trifluoromethyl, amino, hydroxy, acetamido, cyano, carboxy or fluoro; naphthyloxy; morpholino-phenyloxy; 2-hydroxyethylthio; phenylthio; phenylsulphonyl; 4-(2-carboxy-2-amino ethyl)-phenoxy; 2-pyridylthio; 4-pyridylthio; benzyloxy; 3-pyridyl-phenoxy; 3-tetrazolyl-phenoxy; 3,4-methylenedioxy-phenoxy; 3,4-ethylenedioxy-phenoxy; tetrahydroquinolinoxy; quinolinoxy; or quinolinthio.

5. A compound as claimed in claim 1, wherein R₂ is a phenyl group which may be substituted by one or more of hydroxy, halogen, methoxy, methyl, isopropyl, tert-butyl and trifluoromethyl; isopropyl, cyclohexyl; 3-pyridinyl; naphthyl; biphenyl; 2-thienyl; 3,4-methylenedioxyphenyl; 3,4-ethylenedioxy -phenyl; benzothienyl; thiazolyl; quinolinyl; isoquinolinyl; tetrahydroquinolinyl; tetrahydronaphthyl; aminonaphthyl; or acetamidonaphthyl.

6. A compound as claimed in claim 1, wherein R₃ is benzyloxy, 3-phenylpropyloxy, 3-phenylpropyl, 3-phenylprop-1-enyl, 6-N,N-dibenzyloxycarbonyl-guanidino-hexyl, 6-guanidino-hexyl, methoxy-methyleneoxy-methyl, 2-amino-ethoxy-methyl, 3-(pyridin-3- or 4-yl)-propyl, or 3-(pyridin-3- or 4-yl)-prop-1-enyl.

7. A compound as claimed in claim 1, wherein the R and R₁ groups are cis to each other.

8. A compound as claimed in claim 1, selected from the group consisting of:

(3S,4S)-3-[2S-2-(benzyloxycarbonylamino)-2-benzyl]-acetamido-3-methyl-4-phenoxy azetidin-2-one,
(3S,4S)-3-[2S-2-(benzyloxycarbonylamino)-2-isopropyl]-acetamido-3-methyl-4-phenoxy azetidin-2-one,
(3S,4S)-3-[2S-2-(N-benzyloxycarbonyl)-amino-2-isopropyl]-acetamido-3-benzyl-4-phenoxy azetidin-2-one,
(3S,4S)-3-[2S-2-(3-phenylpropionyl)-amino-2-benzyl]-acetamido-3-methyl-4-acetoxy azetidin-2-one,
(3S,4S)-3-[2S-2-(3-phenylpropionyl)-amino-2-benzyl]-acetamido-3-methyl-4-phenoxy azetidin-2-one,
(3S,4R)-3-[2S-2-(3-phenylpropionyl)-amino-2-benzyl]-acetamido-3-methyl-4-acetoxy azetidin-2-one,
(3S,4S)-3-[2S-2-(6-N,N-dibenzyloxycarbonylguanidino hexanoyl)-amino-2-cyclohexylmethyl]-acetamido-3-methyl-4-phenoxy-azetidin-2-one,
(3S,4R)-3-[2S-2-(tert-butoxycarbonyl)-amino-2-cyclohexylmethyl]-acetamido-3-methyl-4-phenoxy-azetidin-2-one,
(3S,4R)-3-[2S-2-(6-N,N-dibenzyloxycarbonylguanidino hexanoyl)-amino-2-cyclohexylmethyl]-acetamido-3-methyl-4-phenoxy azetidin-2-one,
(3S,4S)-3-[2S-2-(6-N,N-di-tert-butoxycarbonylguanidino hexanoyl)-amino-2-cyclohexylmethyl]-acetamido-3-methyl-4-phenoxy-azetidin-2-one,
(3S,4R)-3-[2S-2-(N-benzyloxycarbonyl)-amino-2-benzyl]-acetamido-3-methyl-4-phenoxy azetidin-2-one,
(3S,4S)-3-[2S-2-(N-tert-butoxycarbonyl)-amino-2-(pyridin-3-yl)]-acetamido-3-methyl-4-phenoxy azetidin-2-one,
(3S,4S)-3-[2S-2-(N-benzyloxycarbonyl)-amino-2-(pyridin-3-yl)]-acetamido-3-methyl-4-phenoxy azetidin-2-one,
(3S,4R)-3-[2S-2-(N-tert-butoxycarbonylamino)-2-(pyridin-3-yl)]-acetamido-3-methyl-4-phenoxy azetidin-2-one,
(3S,4S)-3-[2S-2-(N-benzyloxycarbonyl)-amino-2-benzyl]-acetamido-3-methyl-4-acetoxy azetidin-2-one,
(3S,4S)-3-[2S-2-(N-benzyloxycarbonyl)-amino-2-benzyl]-acetamido-3-methyl-4-(benzothiazol-2-yl)-mercapto azetidin-2-one,
(3S,4R)-3-[2S-2-(N-benzyloxycarbonyl)-amino-2-benzyl]-acetamido-3-methy-4-(benzothiazol-2-yl)-mercapto azetidin-2-one,
(3S,4S)-3-[2S-2-(N-benzyloxycarbonyl)-amino-2-benzyl]-acetamido-3-methyl-4-(3-diphenylmethoxycarbonyl)-phenoxy azetidin-2-one, (3S,4S)-3-[2S-2-(3-phenylpropionyl)-amino-2-benzyl]-acetamido-3-methyl-4-(3-diphenylmethoxycarbonyl)-phenoxy azetidin-2-one, (3S,4S)-3-[2S-2-(3-phenylpropionyl)-amino-2-benzyl]-acetamido-3-methyl-4-(3-carboxy)-phenoxy azetidin-2-one, (3S,4S)-3-{2S-2-[5-[-1-piperazine-4-(pyrimidin-2-yl)-5-oxo-pentanoyl)-amino-2-isopropyl]-acetamido-3-methyl-4-phenoxy azetidin-2-one, (3S,4S)-3-[2S-2-(2R-benzyloxycarbonyl)-amino-2-phenyl)-acetamido-2-isopropyl]-acetamido-3-methyl-4-phenoxy azetidin-2-one, and pharmaceutically acceptable salts thereof.

9. A pharmaceutical composition comprising a compound as claimed in claim 1 together with a pharmaceutically acceptable carrier.

10. The compound according to claim 1, wherein the aryl group is a mono-, bi- or tricyclic carbocyclic aromatic group, or a group comprising two covalently linked monocyclic carbocyclic aromatic groups; and the heterocyclic group is a 5–7 membered heterocyclic ring containing one or more heteroatoms selected from S, N and O, optionally fused to a benzene or heteroatom containing ring.

11. A method for treating a disease susceptible to amelioration by inhibition of cathepsin activity in a patient in need of such treatment, comprising administering to the patient an amount of a compound as claimed in claim 1 effective to inhibit such activity, wherein the disease is muscular dystrophy, osteoporosis, rheumatoid arthritis, neuronal or cardiac ischaemia, allergy, or Chagas disease.

12. A compound as claimed in claim 1, selected from the group consisting of:

(3S,4S)-3-[2S-2-(benzyloxycarbonylamino)-2-isopropyl]-acetamido-3-methyl-4-phenoxy azetidin-2-one, (3S,4S)-3-[2S-2-(N-benzyloxycarbonyl)-amino-2-isopropyl]-acetamido-3-benzyl-4-phenoxy azetidin-2-one, (3S,4S)-3-[2S-2-(6-N,N-dibenzyloxycarbonylguanidino hexanoyl)-amino-2-cyclohexylmethyl]-acetamido-3-methyl-4-phenoxy-azetidin-2-one, (3S,4R)-3-(2S-2-(tert-butoxycarbonyl)-amino-2-cyclohexylmethyl]-acetamido-3-methyl-4-phenoxy-azetidin-2-one, (3S,4R)-3-[2S-2-(6-N,N-dibenzyloxycarbonylguanidino hexanoyl)-amino-2-cyclohexylmethyl]-acetamido-3-methyl-4-phenoxy azetidin-2-one, (3S,4S)-3-[2S-2-(6-N,N-di-tert-butoxycarbonylguanidino hexanoyl)-amino-2-cyclohexylmethyl]-acetamido-3-methyl-4-phenoxy-azetidin-2-one, (3S,4S)-3-[2S-2-(N-tert-butoxycarbonyl)-amino-2-(pyridin-3-yl)]-acetamido-3-methyl-4-phenoxy azetidin-2-one, (3S,4S)-3-[2S-2-(N-benzyloxycarbonyl)-amino-2-(pyridin-3-yl)]-acetamido-3-methyl-4-phenoxy azetidin-2-one, (3S,4R)-3-[2S-2-(N-tert-butoxycarbonylamino)-2-(pyridin-3-yl)]-acetamido-3-methyl-4-phenoxy azetidin-2-one, (3S,4S)-3-[2S-2-(N-benzyloxycarbonyl)-amino-2-benzyl]-acetamido-3-methyl-4-(benzothiazol-2-yl)-mercapto azetidin-2-one, (3S,4R)-3-[2S-2-(N-benzyloxycarbonyl)-amino-2-benzyl]-acetamido-3-methy-4-(benzothiazol-2-yl)-mercapto azetidin-2-one, (3S,4S)-3-[2S-2-(3-phenylpropionyl)-amino-2-benzyl]-acetamido-3-methyl-4-(3-diphenylmethoxycarbonyl)-phenoxy azetidin-2-one, (3S,4S)-3-[2S-2-(3-phenylpropionyl)-amino-2-benzyl]-acetamido-3-methyl-4-(3-carboxy)-phenoxy azetidin-2-one, (3S,4S)-3-{2S-2-[5-[-1-piperazine-4-(pyrimidin-2-yl)-5-oxo-pentanoyl)-amino-2-isopropyl]-acetamido-3-methyl-4-phenoxy azetidin-2-one, (3S,4S)-3-[2S-2-(2R-benzyloxycarbonyl)-amino-2-phenyl)-acetamido-2-isopropyl]-acetamido-3-methyl-4-phenoxy azetidin-2-one, and pharmaceutically acceptable salts thereof.

* * * * *